(12) United States Patent
Harr et al.

(10) Patent No.: US 6,723,567 B1
(45) Date of Patent: Apr. 20, 2004

(54) SCREENING METHOD FOR APOPTOSIS AND NECROSIS

(75) Inventors: Thomas Harr, Oberwil (CH); Alessandro Strebel, Basel (CH); Peter Erb, Basel (CH); Sinuhe Hahn, Buckten (CH)

(73) Assignee: Aponetics Ltd., Witterswil (SE)

( * ) Notice: Subject to any disclaimer, the term of this patent is extended or adjusted under 35 U.S.C. 154(b) by 0 days.

(21) Appl. No.: 09/600,148

(22) PCT Filed: Jan. 12, 1999

(86) PCT No.: PCT/IB99/00030

§ 371 (c)(1), (2), (4) Date: Sep. 19, 2000

(87) PCT Pub. No.: WO99/35493

PCT Pub. Date: Jul. 15, 1999

Related U.S. Application Data

(60) Provisional application No. PCT/IB99/00030, filed on Jan. 12, 1999.

(30) Foreign Application Priority Data

Jan. 12, 1998 (EP) ............................................. 98100369

(51) Int. Cl.⁷ ......................... G01N 21/76; G01N 33/48
(52) U.S. Cl. ............................. 436/172; 436/63; 436/64; 436/517; 436/537; 436/546; 436/7.2; 436/7.23; 436/7.8; 436/8; 436/7.72; 436/69.1; 436/172.2; 436/172.3; 436/375; 436/377; 436/384; 436/252.3; 436/254.11
(58) Field of Search ................... 435/7.1, 7.4, 7.72, 435/7.23, 69.1, 7.2, 183, 7.8, 320.1, 8, 375, 377, 252.3, 384, 254.11, 172.2, 172.3; 436/63, 64, 517, 537, 546, 172; 536/23.1, 23.4, 23.5; 530/324, 350; 514/44

(56) References Cited

U.S. PATENT DOCUMENTS

| | | | |
|---|---|---|---|
| 5,945,291 A | * | 8/1999 | Bolton et al. ................ 435/7.1 |
| 5,958,713 A | * | 9/1999 | Thastrup et al. ............. 435/7.4 |
| 6,172,188 B1 | * | 1/2001 | Thastrup et al. ............ 530/350 |
| 6,207,801 B1 | * | 3/2001 | Alnemri ..................... 530/350 |

FOREIGN PATENT DOCUMENTS

| | | |
|---|---|---|
| EP | 0 806 668 A2 | 11/1997 |
| WO | WO 95/27903 | 10/1995 |
| WO | WO 97/11094 | 3/1997 |
| WO | WO 97/14812 | 4/1997 |

OTHER PUBLICATIONS

Cormack et al., "FACS–optimized mutants of the green fluorescent protein (GFP)," *Gene*, 173(1):33–38 (1996).

Lamm et al., "A rapid, quantitative and inexpensive method for detecting apoptosis by flow cytometry in transiently transfected cells," *Nucleic Acid Research*, 25(23):4855–4857 (1997).

Li et al., "Use of Green Fluorescent Protein in Studies of Apoptosis of Transfected Cells," *BioTechniques*, 23(6):1026–1029 (1997).

* cited by examiner

*Primary Examiner*—Christopher L. Chin
*Assistant Examiner*—Gailene R. Gabel
(74) *Attorney, Agent, or Firm*—Marshall, Gerstein & Borun LLP

(57) ABSTRACT

The present invention relates to a method for the determination of non-, anti-, or pro-apoptotic and necrotic conditions of cells, newly designed vectors coding for marker proteins, cell lines transfected with such vector, and a method to assay the non-, pro- or anti-apoptotic or necrotic activity of test compounds.

21 Claims, 16 Drawing Sheets

SCREENING METHOD FOR APOPTOSIS AND NECROSIS

CROSS REFERENCE TO RELATED APPLICATION

This application is a national stage application under 35 U.S.C. §371 of International Application No. PCT/IB99/00030, filed Jan. 12, 1999, which cliams priority from European Patent Application Ser. No. EP 981 00 369.2 filed Jan. 12, 1998, and also is a continuation of this application under 35 U.S.C. §120.

FIELD OF THE INVENTION

The present invention relates to a method for the determination of non-, anti-, or pro-apoptotic and necrotic conditions of cells, using newly designed vectors coding for marker proteins, cell lines transfected with such vector, and a method to assay the non-, pro-, or anti-apoptotic or necrotic activity of test compounds or physical stimuli.

BACKGROUND ART

Apoptosis plays an essential role in development, i.e. embryogenesis and normal cell turnover, but also in diseases such as cancer, AIDS, neurodegeneration and viral infections. Unlike necrosis, apoptosis is an active, gene-directed self-destruction process of the cell and is associated with characteristic morphological and biochemical changes[1,2]. Nuclear and cytoplasmic condensation and fragmentation of the dying cell into membrane-bound apoptotic bodies are typical characteristics of apoptosis. Another feature of apoptotic cell death is the chromosomal DNA degradation into oligonucleosomal fragments after the activation of specific nucleases[3,4].

Apoptosis can be induced by the interaction of the cell surface molecule Fas (CD95) with Fas-Ligand (FasL), where the Fas expressing and sensitive cells undergo apoptosis. Fas is a type I membrane protein, which belongs to the tumor necrosis factor (TNF) and nerve growth factor (NGF) receptor family[5-7]. Fas expression is found on a wide variety of tissues and cells such as thymus, liver, lung, ovary, heart and myeloid cells[9-12]. FasL expression is not only found on lymphocytes but also on a wide variety of tissues and some tumors[13-19]. Both membrane bound FasL and the soluble form (sFasL) can induce apoptosis in Fas positive and sensitive cells. Other forms among a variety of apoptosis mediators include the Perforin/Granzyme system, the TRAIL/TRAIL-R system[36], cytokine deprivation (e.g. IL-3 deprivation) and irradiation.

In contrast to apoptosis, necrosis is a non-physiological death of cells due to chemical or physical injury of the cell membrane. Morphological criteria include cell swelling and cell lysis, lysosomal leakage and loss of the cell membrane integrity.

During the last decade, it has become clear that apoptosis plays a keyrole in several diseases. Apoptosis is increased in AIDS, but decreased in cancer and certain autoimmune proliferative diseases.

Flow cytometry offers a wide variety of possibilities to measure apoptosis. Different methods have been established and implemented, some which stain on the cell surface and some which stain intracellularily.

One of the first approaches was, beside the observation that apoptotic cells shrink and have higher intracellular granularity, to stain with DNA specific fluorochromes (e.g. propidium iodide [PI], ethidium bromide [EtBr]). As soon as a lethal hit is being induced, the DNA starts. to change its profile. Apoptotic DNA not only consists of fragmented DNA (visualised as shorter bands, so called DNA ladder, in an agarose gel) but is also partially digested into single nucleotides, so that fluorochromes, like PI or EtBr, have less DNA to stain. This is typically observed by a shift to the left, called sub-G1 peak, on the specific fluorochrome detection channel in the FACScan™ (from Becton Dickinson, USA). The big disadvantage of this method is that the cell membranes have first to be permeabilized with reagents, like ethanol, in order to stain them with DNA specific dyes, like PI[20]. The treatment is time and labour consuming, and the risks of loosing cells and of handling errors are high. Furthermore, the discrimination between live and apoptotic cells cannot be standardised and requires large experience.

Another method is the terminal deoxynucleotidyl transferase (TdT)-mediated endlabeling of the DNA strand breaks (TUNEL). The TUNEL method detects DNA strand breaks in cells undergoing apoptosis. TdT is an enzyme which catalyzes the addition of deoxyribonucleotide triphosphate to the 3'-OH ends of double or single-stranded DNA. Unlike normal cells, apoptotic cell nuclei incorporate exogenous nucleotides (dUTP)-DIG in the presence of TdT. An anti-DIG antibody fragment with a conjugated fluorochrome enables the visualisation of apoptotic cells. An increase of apoptotic cells causes a higher number of DNA fragments and consequently a brighter fluorescence. An advantage of this method is the very high specificity[21]. A disadvantage of this method is that it is expensive and can only be used for a small set of samples, because it is time intensive. Therefore, it is not applicable for large screening programmes.

The loss of cell membrane polarity and the presentation of increased amounts of phosphatidyl serine (PS) on the outside of the cell membrane during the early phase of apoptosis has led to yet a new approach. Annexin V is a calcium-dependent phospholipid binding protein with high affinity for PS. Due to the fact, that the cell membrane integrity is maintained in the early and intermediate phases of apoptosis but not in necrosis, it is possible to distinguish between apoptotic and necrotic cells, when Annexin V is used concomitantly with the DNA dye PI. Early and intermediate apoptotic cells show increased binding of Annexin-FITC and are mainly negative for PI-staining. Late apoptotic stages and necrotic cells become double positive, because of PS presentation on the surface and the PI staining of intracellular nucleic acids due to disintegration of the membrane[22]. This method is also costly and labour intensive.

Green fluorescence protein (GFP) from the jellyfish *Aequorea victoria* can be used to monitor gene expression and protein localization in living organisms (in vivo) and in vitro[23-26]. GFP-fluorescence is stable, can be monitored noninvasively in living cells and persists in paraformaldehyde-fixed cells. FACS-optimized mutants of green fluorescence protein have been developed[8]. One of these mutants (GFPmut1) has been integrated into the PEGFP vectors and is commercially available (from Clontech). The big advantage of this mutant is that the maximal excitation peak of GFPmut1is 488 nm and the emission maxima is 507 nm. Conventional flow cytometers are equipped with an argon laser emitting light at 488 nm and have the suitable detection filters already installed, making the GFPmut1-protein an ideal candidate for flow cytometry studies and fluorescence microscopy.

GFP has already been used as marker for visualizing changes in cell morphology such as blebbing caused by cytotoxic agents or apoptosis, or as transfection marker (WO97/11094), or as marker for screening factors modulating gene expression (WO97/14812). GFP has also been used as a marker protein to detect the progression of the morphological changes of apoptotic cells[37].

GFP has been used as a marker protein to detect cells transiently transfected with the commercially available plasmid pEGFP-C1 (Clontech)[34]. According to Lamm et al.[34] apoptosis was detected by reduced fluorescence of the DNA-binding dye PI in the apoptotic subpopulation. It was not recognized that GFP itself could be used as a marker for apoptosis. The great disadvantage of PI-staining is that no changes in the state of one and the same cells can be monitored but only one specific state since for PI-staining the cells have to be permeabilized and fixed.

Experiments by the present inventors have shown, that stable transfection of eukaryotic cells (e.g. A20.2J) with the pEGFP-C1 (as received from the manufacturer Clontech with the cytomegalovirus CMV promoter) used in the above cited state of the art for tansient transfection results in little or no expression of the GFPmut1gene.

For the foregoing reason there is a need for a new and improved method and tools for determining apoptosis and necrosis of cells which in particular can be used to efficiently and cheaply assay compounds on their pro-apoptotic or anti-apoptotic or necrotic activity.

DISCLOSURE OF THE INVENTION

Accordingly, objects of the invention are to provide an improved method for the determination of apoptosis and/or necrotic conditions of cells and to provide improved tools useful for this method.

The present invention is directed to a method for the determination of apoptotic and/or necrotic conditions of living test cells that satisfies the hereinbefore discussed needs. This method comprises monitoring changes in the signal or the intensity, respectively, of a marker protein in said test cells, in particular a method wherein the apoptotic and/or necrotic condition is monitored in the presence of a non-, pro- or anti-apoptotically or necrotically active compound, and/or a physical stimulus, and wherein the marker protein is preferrentially produced in the test cells after stable transfection of said cells with a DNA coding for and expressing the marker protein.

Preferred marker proteins are fluorescent marker proteins with the Green Fluorescent Protein (GFP) or a fluorescent mutant thereof, e.g. GFPmut1, being particularly preferred.

Another object of the present invention is a new vector for the transfection, preferably the stable transfection of test cells which are able to highly express said marker protein, preferably a fluorescent protein, in particular GFP or a mutant thereof. It was found that the known hEF-1α promoter, and the new combination of the CMV and the MoLV-LTR promoter are particularly well suited for enhancing transcription of the GFPmut1 gene.

Another object of the present invention are live cells or live cell lines, respectively stably transfected with such a vector. Such a cell line can be used in an assay to determine non-, pro- or anti apoptotic or necrotic activity of test compounds. Although it is possible to transfect live cells with more than one vector with different marker molecules, for e.g. the simultaneous detection of different signals, usually one marker is sufficient.

Another object of the present invention is a method to assay the non-, pro or anti-apoptotic or necrotic activity of a test compound on live test cells. This method comprises stably transfecting a group of said cells with at least one vector coding for and expressing a marker protein. The transfected cells are treated in a suitable culture medium with a test compound. The change in the signal or intensity of a signal, respectively, i.e. the decrease or increase, of the expressed marker protein in said group of cells is monitored by conventional methods, and compared with the results observed with a parallel group of the same test cells which was not exposed to the test compound but otherwise identically treated. The test compound may consist of a multiplicity of compounds, e.g. as obtained from combinatorical chemistry methods. Of particular interest are the apoptotic or necrotic conditions of normal and cancer cells under the influence of test compounds and/or physical stimuli.

In a specific embodiment of the methods of the present invention the test cells or cell line are transfected with a test gene expressing a protein of interest such as an apoptosis inhibitor or an apoptosis stimulator.

These and other features, aspects, and advantages of our invention will become better understood with reference to the following description of modes for carrying out the invention, the appended claims and accompanying drawings.

MODES FOR CARRYING OUT THE INVENTION

Figure 1:
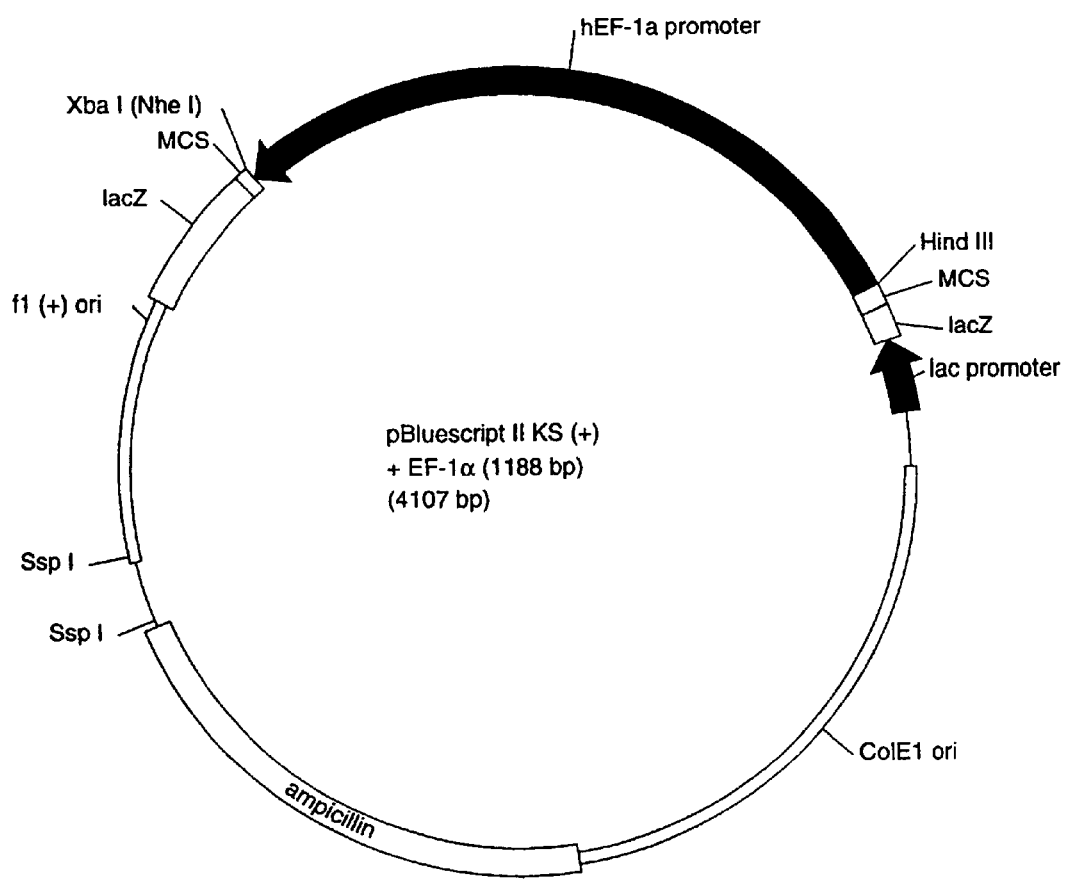
FIG. 1: pBluescriptIIKS(+)+EF-1α plasmid. The promoter of human EF-1α has been cloned into the pBluescriptIIKS (+)vector (from Stratagene) with Hind III and Xba I.

Apoptotic and/or necrotic conditions of cells can be induced either physically, e.g. by irradiation, or chemically, e.g. by treatment with pro-apoptotically or necrotically or other active compounds.

Marker proteins, that can be used for the method, are proteins which are detectable by their physical and/or chemical characteristics, e.g. by fluoresence, thereby allowing the measurement of a signal at at least two different times, i.e. a change in the signal. Suitable marker proteins furthermore have to change their signal dependent on the live and apoptotic and/or necrotic state of the cells. They can be directly introduced into the cells or produced internally after transfection with a vector expressing the marker protein. Direct introduction of the marker protein may be achieved by methods known in the art, e.g. by the use of liposomes. Test cells are transfected either transiently, e.g. with a lipid such as the LipofectAMINE™ reagent, or preferentially stably by use of a gene-gun or other suitable methods, and preferably by electroporation or with the SuperFect Reagent. Useful vectors are of RNA or preferably of DNA origin. The marker protein is produced in the test cells after transfection with the vector, usually a DNA vector, coding for and expressing the marker protein. Useful marker proteins are known and comprise any detectable proteins, in particular fluorescent proteins, e.g. the blue fluorescent protein (BFP), a green fluorescent protein such as GFPuv or GFPwt. A preferred marker protein is the GFPmut1.

The amount of intact marker protein (marker function) present in the cells can be visualized by the physical and/or chemical characteristics or interactions of the marker protein, preferably by fluorescence. Under necrotic conditions the marker protein loses its function much faster and more completely compared to apoptotic conditions. Under necrotic conditions the marker function is lost within a few hours (usually 100% necrosis is obtained within 1 to 2 hours), whereas functional loss is delayed under apoptotic conditions. Contrary to necrosis, apoptosis is dependent on the specific cell line and the specific apoptosis inducer, and usually takes 8 hours or more. The difference in time also allows the distinction between these two cell conditions.

Useful visualisation is performable on live cells, preferably on live cells in the culture medium either by color reactions or preferentially by fluorescence measurements. Detection devices comprise flow cytometry, e.g. FACScan™, fluorescence platereaders, e.g. FLIPRT™, or any other suitable detection device. The acquisition device used is a FACScan™. The following parameters are preferentially measured:

FSC-Height (forward scatter) as a measure for the cell size,

SSC-Height (side scatter) as a measure for the internal granularity (density) of the cells, green fluorescence (e.g. of GFPmut 1) is visualised on the FL-1 channel (FL-1 Height) in the FACScan™.

The results are compared after dot plot and/or histogramm visualisation (see FIGS. 4 to 15).

Useful test cells comprise eukaryotic and prokaryotic cells. Prokaryotic cells include bacterial and cyanobacterial cells. Eukaryotic cells include mammalian, fungal, insect, avian, worm, fish, crustacean, reptilian, amphibian and plant cells as well as cell lines thereof. The test cells usable in the method are cells of any type, preferentially normal, i.e. genetically non-altered, infected, e.g. with virus, parasites, bacteria or prions infected, tumor cells or genetically manipulated or altered cells of human or animal origin, which can be cultured in vitro, carrying a vector expressing the marker gene, but also marker gene transformed bacteria that can be used in antibiotics screening. Such test cells are for example lymphoma cells, e.g. A20.2J, Jurkat, mast cells, e.g. PB-3c, or melanoma cells, e.g. DM, which are transfected with DNA vectors pBluescriptIIKS(+)+EF-1α+EGFP or pEGFP-N 1 +MoLV-LTR, respectively, to give the live cell lines named A20GFP, PB3cGFP, JurkatGFP or DMGFP, respectively.

It was found that transcription and translation modulation, e.g. inhibition, is insignificant to the method of the present invention.

For the same reason also direct introduction of marker protein or expression of marker protein in transiently transfected cells leads to good results.

Figure 16:
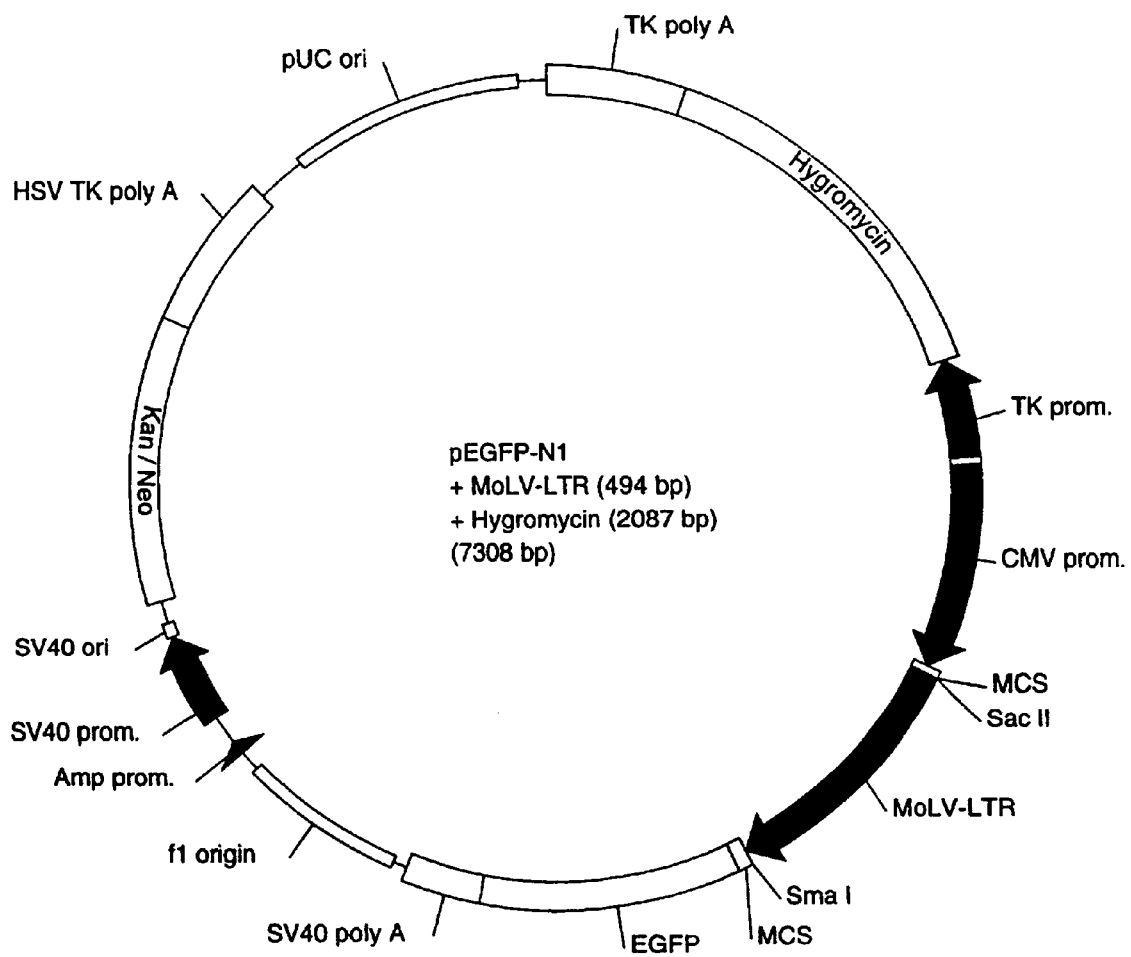
FIG. 16: pEGFP-N1+MoLV-LTR plasmid containing a hygromycin gene (from pREP4, Invitrogen). The MoLV-LTR promoter (from pLXSN, Clontech) has been cloned into the pEGFP-N1 vector (from Clontech) with Sma I and Sac II. The hygromycin gene (from pREP4 digested with Nru I) has been cloned into the Ase I predigested pEGFP-N1+MoLV-LTR vector.

However, for studies including reproducibility studies it is much preferred to use stably transfected cell lines. Stably transformed cell lines that are highly and stably expressing over long times are obtainable with the above mentioned DNA vectors pBluescriptIIKS (+)+EF-1α+EGFP and pEGFP-N1+MoLV-LTR or variants thereof comprising further selection markers such as a hygromycin encoding gene (see e.g. FIG. 16) and/or a gene expressing a protein to be examined, e.g. a possible or known apoptosis inhibitor or stimulator.

With stably transfected cell lines comprising one of the above mentioned vectors, very reliable and very good reproducible results were obtained with differences in the % range detectable.

In a preferred method the presence of Green Fluorescent Protein (GFP) or a fluorescent mutant thereof (e.g. GFPmut1) is monitored by means of a flow cytometer measuring the fluorescence intensity. In general two groups of test cells are used, each of a defined number of cells (e.g. cancer cells), which are transfected with a DNA vector according to our invention. Depending on the detection device the number of test cells in the test tubes is 1 to 50,000,000, usually 5 to 50,000,000, but for flow cytometry 10,000 to 500,000 are preferably used. In a preferred method two groups of test cells are used, each of a defined number of cells (e.g. cancer cells), which are stably transfected with any of the vectors according to the invention, incubating one group together with the test compound in a culture medium, stimulating the cells of both groups with an excitation beam, usually with a wave length of high energy, in particular an argon laser, determining the fluorescing intensity of the cells of each group by means of a flow cytometer, presently on the FL-1 channel (FL-1 Height), and comparing the obtained fluorescing intensity of the cells of the two groups.

Another embodiment of the invention is directed to vectors, useful in the method described above. A vector according to the invention comprises a gene coding for the marker protein which is operably linked to one or more strong promoters, preferably the hEF-1α promoter, the MoLV-LTR promoter or a combination of the CMV and the MoLV-LTR promoter. The promoter of EF-1α (elongation factor-1α) chromosomal gene efficiently stimulates in vitro transcription[28]. EF-1α promotes the GTP-dependent binding of an aminoacyl-tRNA to ribosomes in eukaryotic cells. EF-1α is one of the most abundant proteins in eukaryotic cells and is expressed in almost all kinds of mammalian cells. The MoLV-LTR (Moloney Leukemia Virus-Long Terminal Repeat) is a very effective promoter[33]. These findings make the promoter of EF-1α and the MoLV-LTR promoter preferred candidates for enhancing transcription of a desired gene.

Preferred vectors have a gene coding for the GFP or a fluorescent mutant thereof. They are in particular able to express the marker protein GFPmut1. Such vectors are specifically the plasmid pBluescript II KS(+)+EF-1α+EGFP and pEGFP-N1+MoLV-LTR.

Advantageously vectors with one or more strong promoters are used in order to obtain a high expression of the gene coding for the marker protein, preferably GFPmut 1.

The present vectors are produced by methods known in the art.

Another embodiment of the invention is directed to live cell lines useful in the above method. Preferred living cell lines are transfected with a preferred vector according to the invention and are named A20GFP, PB3cGFP, JurkatGFP or DMGFP.

A20.2J is preferentially transfected with the pBluescriptIIKS(+)+EF-1α+EGFP vector, whereas Jurkat, PB-3c, and DM are transfected with the pEGFP-N 1+MoLV-LTR vector. Suitable methods to transfect cells are known to the skilled person and are e.g. electroporation or with the SuperFect Reagent. The transfected cells are selected by single cell assay in order to obtain clonally and stably transfected cell lines. The selection process involves high GFP expression (high fluorescence intensity) and GFP-fluorescence of the selected cells in a narrow range, in order to obtain a homogenous high GFP-expressing cell line.

Cells or cell lines suitable for the methods of the present invention are also cells or cell lines transfected with a test gene, i.e. a gene the effect of which on apoptosis or apoptotic conditions shall be studied such as apoptosis inhibitors or stimulators, also called anti-apoptotic or pro-apoptotic genes. Such cells or cell lines are also suitably usable in drug screening methods or to determine the effect of test substances applied to such cells or cell lines.

Anti-apoptotic genes are for example bcl-2, bcl-$X_L$ and FLIP (FLICE inhibitory protein), and pro-apoptotic genes are for example bax, bcl-$X_S$ and bad.

Methods and vectors to produce transfected cells are known to the skilled person and are applicable for the production of cells or cell lines, respectively, that are suitable for the present invention and transfected with an anti-apoptotic or pro-apoptotic gene. Whereas for the transfection with GFP the vectors of the present invention are preferred, the transfection with anti-apoptotic or pro-apoptotic genes can be performed with any vector suitable for, preferably stable, transfection.

In another embodiment the invention is directed to an assay to determine the non-, pro-, or anti-apoptotic or necrotic activity of new or known test compounds. The test is performed in that a defined number of transfected and selected cells is incubated with a test compound or/and a physical stimuli, e.g. sonication or irradiation, in the appropriate culture medium. Preferentially 250,000 cells per condition are used. Any culture medium can be used in which the cells survive and/or grow. Preferred culture media comprise e.g. Iscove's for A20GFP and DMGFP, Iscove's plus IL-3 for PB3cGFP, and RPMI for JurkatGFP.

For comparative and standardisation purposes useful apoptotic compounds are e. g. proteins, such as FasL, fatty acids, e.g. ceramide, steroids, e.g. cortisol, antibiotics, e.g. bleomycin, and others. A preferred apoptotic substance for A20GFP is FasL. A preferred apoptotic substance for JurkatGFP is FasL or TRAIL. A useful anti-apoptotic substance for PB3cGFP is IL-3. Toxicity and thereby necrosis can be induced with a wide variety of substances. Preferred induction of necrosis includes the use of antibodies plus complement on A20GFP.

Cells can be cultured at different temperatures, but for the assay the test cells are preferably cultured at 37° during the time of the assay. In FACS-analysis 10,000 cells are usually evaluated from a pool of 250,000 cells.

Live, transfected cells, in comparison to apoptotic transfected cells, show a high level of specific fluorescence intensity, whereas apoptotic cells lose part of their fluorescent capacity after some hours (shift to the left on the fluorescence detecting channel FL-1). On the other hand, necrotic cells lose all their fluorescing capacity within a couple of hours and at that time render them indistinguishable from non-transfected cells.

The reduction of the experimental set-up to a single parameter (a marker protein, e. g. GFPmut1) and the possibility of standardisation renders the present invention a useful and improved method for the screening of non-, pro-, antiapoptotic and necrotic substances and/or physical stimuli. Standardisation is possible for the transfection and selection method, the fluorescence measuring, the numbers of transfected cells, the amount of test compounds used, the type and intensity of the physical stimuli, and other standardizable parameters, such as the setup of the flow cytometer and/or any other suitable screening device, e. g. fluorescence platereaders.

Although the present invention has been described in considerable detail with reference to certain preferred embodiments thereof, it should be noted that other embodiments or versions are possible. For example for the detection of the effect of non-, pro- or anti apoptotically or necrotically active compounds on specific cell lines, e.g. specific cancer cell lines, such as cell lines of malignant tumors of human breast, lung, brain, colon, prostate and the like, the relevant cell line may be stably transfected with a vector of the invention, or vectors encoding other easily detectable proteins may be constructed and used for transfection. Therefore the spirit and scope of the appended claims should not be limited to the description of the preferred versions contained therein.

The following examples describe the invention in still more detail but they also should not be construed as a limitation of the present invention.

EXAMPLE 1

Construction of pBluescriptIIKS(+)+EF-1α+EGFP

Figure 2:
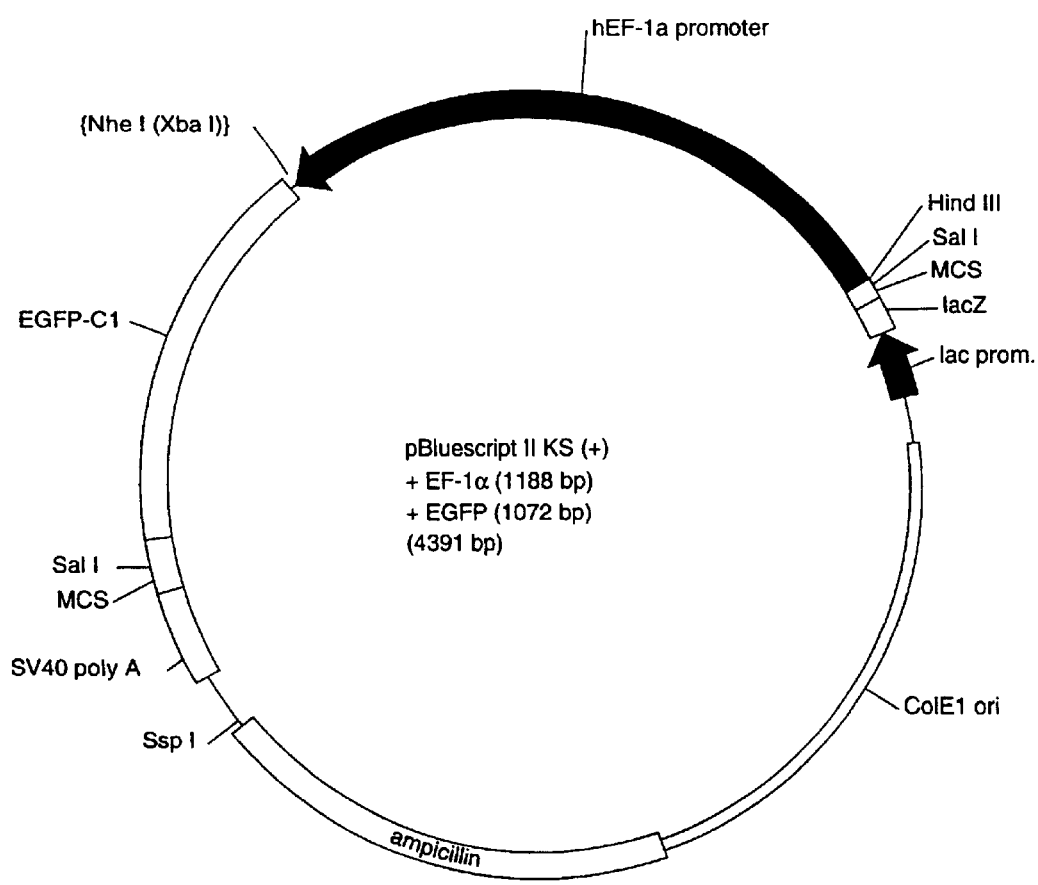
FIG. 2: pBluescriptIIKS(+)+EF-1α+GFP plasmid. The gene coding for GFPmut1 (from pEGFP-C1, Clontech) has been cloned into the pBluescriptIIKS(+)+EF-1α plasmid with Xba I and Ssp I.

For the construction of the pBluescriptIIKS(+) +EF-1α+ EGFP plasmid (see FIG. 2) the promoter of human EF-1α (from pEF-BOS, kindly provided by S. Nagata[27]) and the gene EGFP+SV40 poly A coding for GFPmut1 (from pEGFP-C1, Clontech) were cloned into the pBluescriptIIKS (+) vector (from Stratagene).

The first step was to clone the promoter of human EF-1α (from pEF-BOS) into the Xba I and Hind III predigested pBluescriptIIKS(+) vector.

The resulting EF-1α promoter fragment, after Hind III and Xba I digestion of pEF-BOS, has a length of 1188 bp, whereas the other resulting fragment corresponds to the pEF-BOS backbone.

The pBluescriptIIKS(+) contains a unique Xba I restriction site (position 677) and a unique Hind III restriction site (position 719). The two resulting fragments after Xba I and Hind III digestion have a length of 2919 bp and 42 bp, respectively.

Three µg pEF-BOS vector were mixed in an Eppendorf tube (tube a) with 1 pl Hind III (from Boehringer Mannheim, 12 U/µl), 1 µl Xba I (from New England Biolabs, 20000 U/ml), 3 µl 10× incubation buffer for restriction enzyme B (from Boehringer Mannheim) and 20 µl double distilled water making a final volume of 30 µl. In another Eppendorf tube (tube b), 3 µg pBluescript II KS(+) were pipetted together with 1 µl Hind III, 1 µl Xba I, 3 µl 10× incubation buffer for restriction enzyme B and 20 µl double distilled water to make a final volume of 30 µl. Both Eppendorf tubes (tubes a and b) were incubated for 3 hours at 37° C. After incubation, 11 µl DNA-loading buffer (0.25% bromophenol blue from Sigma, 0.25% xylene cyanol from Sigma and 15% Ficoll type 400 from Pharmacia in water) were added to both tubes and thereafter the contents were loaded onto separate slots on a 0.6% low-melting-point (LMP) agarose (from Bethesda Research Laboratories) gel. In a third slot, 9 µl 1 Kb DNA-ladder (from Promega), diluted 1:3 with DNA-loading buffer, were loaded on the gel. The 0.6% LMP agarose gel is prepared by mixing 0.3 g LMP-agarose in 50 ml 1× TAE (50× TAE concentrated stock solution (per liter): 242 g Tris (hydroxymethyl)-aminomethane (from Merck), 57.1 ml glacial acetic acid (from Merck), 100 ml 0.5 M EDTA (from Sigma) (pH 8.0) and double distilled water to a final volume of 1 liter), heating the mixture until it is dissolved and adding ethidiumbromide solution (from Sigma) to a final concentration of 1 µg/ml. The gel is run at 60–70 Volts for 60–90 minutes. The ethidiumbromide stained DNA-bands in the gel are visualized with 300 nm UV-light and their size are determined relative to the 1 Kb DNA-ladder. The DNA-band containing the 1188 bp long fragment (EF-1α promoter) from the digested pEF-BOS vector and the DNA-band containing the 2919 bp long fragment from the digested pBluescript II KS(+) were cut out from the LMP agarose gel and put into two different Eppendorf tubes. Both tubes were centrifuged briefly and incubated at 65° C. for 5 minutes. Afterwards, 3.5 µl of the 2919 bp long fragment (Hind III and Xba I digested pBluescript II KS(+)) were mixed together with 7 µl of the 1188 bp long fragment (EF-1α promoter from the Hind III and Xba I digested pEF-BOS) in a separate Eppendorf tube, incubated at 65° C. for 5 minutes and centrifuged briefly. The mixture was cooled at 37° C. and then the following ligation mix was added: 2 µl 10× ligation buffer (from Appligene, provided with T4 DNA ligase), 7.5 µl double distilled water and 1 µl T4 DNA ligase (from Appligene, 5 U/µl). The ligation reaction was incubated overnight at 15 ° C.

The newly ligated pBluescriptIIKS(+)+EF-1α was transformed into One Shot™ competent *E. coli* (from Invitrogen), according to the manufacturer protocol of Invitrogen.

10 µl of the ligation reaction were used for the transformation of competent *E. coli*. 50, 100 and 200 µl of the transformation mixture were plated on different ampicillin-containing LB agar plates (10 g tryptone, 5 g yeast extract, 10 g NaCl, 20 g bactoagar (from Difco Laboratoires Detroit Mich. USA), adjust pH to 7.0 with NaOH, water to a final volume of 1 liter, autoclave, cool the agar-media to 55° C., add ampicillin solution to a final concentration of 50 µg/ml and pour the plate with 10–15 ml agar/plate). The plates/transformation mix were then incubated at 37° C. overnight. The next day different bacterial colonies were picked for further analysis of recombinant DNA clones by small-scale plasmid DNA isolation (according to the alkaline lysis method described in Maniatis et al.[32]).

To check the presence of the EF-1α promoter fragment cloned into pBluescript II KS(+), a Hind III and Xba I restriction enzyme digestion of the isolated DNA was carried out (3 µl 10× incubation buffer for restriction enzyme B, 5 µl plasmid DNA from the alkaline lysis method, 22 µl double distilled water, 1 µl Hind III, 1 µl Xba I were mixed together in an Eppendorf tube and incubated for 3 hours at 37° C.), loaded on a 1% agarose (from Bio-Rad) gel and subsequently visualized with 300 nm UV-light and analyzed. The expected fragment of 1188 bp length after Hind III and Xba I digestion was observed, and therefore confirmed the presence of the cloned fragment (see also FIG. 1).

In order to obtain large quantities of the newly created plasmid, a large-scale plasmid DNA isolation has been performed according to the Qiagen Plasmid Maxi Protocol.

The second step was to clone the EGFP+SV40 poly A (from pEGFP-c1) into the Xba I and Ssp I predigested pBluescript II KS(+)+EF-1α.

The pEGFP-C1 vector (from Clontech) contains a unique Nhe I restriction site (position 592) and two Ssp I restriction sites (position 1664 and 2217). The three resulting fragments, after Nhe I and Ssp I digestion, have a length of 3106 bp, 1072 bp and 553 bp, respectively.

The pBluescriptIIKS(+)+EF-1α (see FIG. 1) contains an Xba I and two Ssp I restriction sites and the three resulting fragments, after Xba I and Ssp I digestion, have a length of 3319 bp, 658 bp and 130 bp, respectively.

Of the pEGFP-C1 vector 4.2 μg were mixed in an Eppendorf tube (tube 1) with 1 μl Nhe I (from New England Biolabs, 4000 U/ml), 1 μl Ssp I (from Boehringer Mannheim, 10 U/μl), 3 μl 10× incubation buffer for restriction enzyme M (from Boehringer Mannheim) and 18 μl double distilled water making a final volume of 30 μl. In another Eppendorf tube (tube 2), 3–4 μg pBluescriptIIKS (+)+EF-1α were pipetted together with 1 μl Xba I, 1 μl Ssp I, 3 μl 10× incubation buffer for restriction enzyme H (from Boehringer Mannheim) and 18 μl double distilled water to make a final volume of 30 μl. Both Eppendorf tubes (tubes 1 and 2) were incubated for 4 hours at 37° C. After incubation, 11 μl DNA-loading buffer were added to both tubes and thereafter the contents were loaded into separate slots on a 0.6% low-melting-point (LMP) agarose gel. In a third slot, 9 μl 1 Kb DNA-ladder, diluted 1:3 with DNA-loading buffer, were loaded on the gel. Run the gel at 60–70 Volts for 60–90 minutes. The ethidiumbromide stained DNA-bands in the gel are visualizd with 300 nm UV-light and their sizes are determined relative to the 1 Kb DNA-ladder. The DNA-band containing the 1072 bp long fragment from the digested pEGFP-C1 vector and the DNA-band containing the 3319 bp long fragment from the digested pBluescript II KS(+)+EF-1α were cut out from the LMP agarose gel and put into two different Eppendorf tubes. Both tubes were centrifuged briefly and incubated at 65 ° C. for 5 minutes. Afterwards, 3.5 μl of the 3319 bp long fragment (Xba I and Ssp I digested pBluescript II KS(+)+EF-1α) were mixed together with 7 μl of the 1072 bp long fragment (EGFP+SV40 poly A from the Nhe I and Ssp I digested pEGFP-C1) in a separate Eppendorf tube, incubated at 65 ° C. for 5 minutes and centrifuged briefly. The mixture was cooled at 37° C. and then the following ligation mix was added: 2 μl 10× ligation buffer, 7.5 μl double distilled water and 1 μl T4 DNA ligase. The ligation reaction was incubated overnight at 15° C.

The newly ligated pBluescriptIIKS(+)+EF-1α+EGFP was transformed into One Shot™ competent *E. coli* (from Invitrogen), according to the manufacturer protocol of Invitrogen. Ten μl of the ligation reaction were used for the transformation of competent *E. coli*. 50, 100 and 200 μl of the transformation mixture were plated on different ampicillin-containing LB agar plates and incubated at 37° C. overnight. The next day different bacterial colonies were picked for further analysis of recombinant DNA clones by small-scale plasmid DNA isolation (according to the alkaline lysis method described in Maniatis et al.[7]).

The newly constructed pBluescript IIKS(+)+EF-1α+EGFP vector (see FIG. 2) contains two Sal I restriction sites, one in the pBluescriptIIKS(+) backbone and the other one in the cloned EGFP+SV40 poly A fragment. The two resulting fragments after a Sal I digestion have a length of 1981 bp and 2410 bp, respectively.

In order to check the presence of the EGFP+SV40 poly A fragment cloned into pBluescriptIIKS(+)+EF-1α, a Sal I restriction enzyme digestion of the isolated DNA was carried out (3 μl 10× incubation buffer for restriction enzyme H, 5 μl plasmid DNA from the alkaline lysis method, 22 μl double distilled water, 1 μl Sal I (from Appligene, 10 U/μl) were mixed together in an Eppendorf tube and incubated for 3 hours at 37° C.), loaded on a 1% agarose gel and subsequently visualized with 300 nm UV-light and analyzed. The two expected fragments of 1981 bp and 2410 bp length after Sal I digestion were observed, and therefore confirmed the presence of the cloned fragment.

In order to obtain large quantities of the newly created plasmid (see FIG. 2), a large-scale plasmid DNA isolation has been performed according to the Qiagen Plasmid Maxi Protocol.

At this point, to check the functionality of the newly constructed pBluescriptIIKS(+)+EF-1α+EGFP plasmid, COS-1 cells (COS-1 is a fibroblast-like cell line established from CV-1 simian cells (ATCC CCL 70), from ATCC CRL 1650) were transiently transfected with 2 μg of the plasmid, according to the DEAE-Dextran Transfection Protocol from the Mammalian Transfection Kit of Stratagene. After 1–3 days incubation at 37° C., the transiently transfected COS-1 cells were analyzed under the fluorescence microscope and highly fluorescing GFP-positive COS-1 cells have been observed, indicating that the constructed GFP-carrying plasmid was functional.

EXAMPLE 2

Construction of pEGFP-N1+MoLV-LTR

Figure 3:
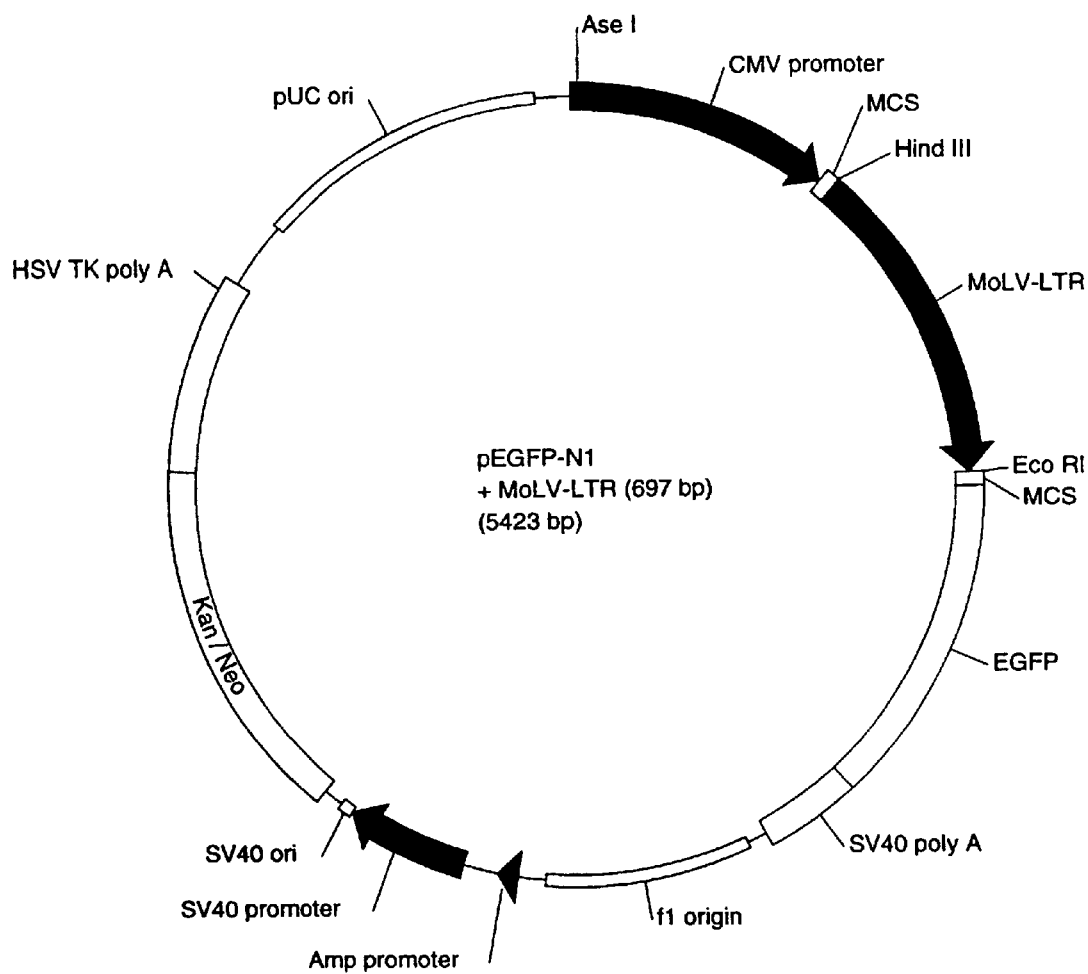
FIG. 3: pEGFP-N1+MoLV-LTR plasmid. The MoLV-LTR promoter has been cloned into the pEGFP-N1 vector (from Clontech) with Hind III and Eco RI.
Figure 4:
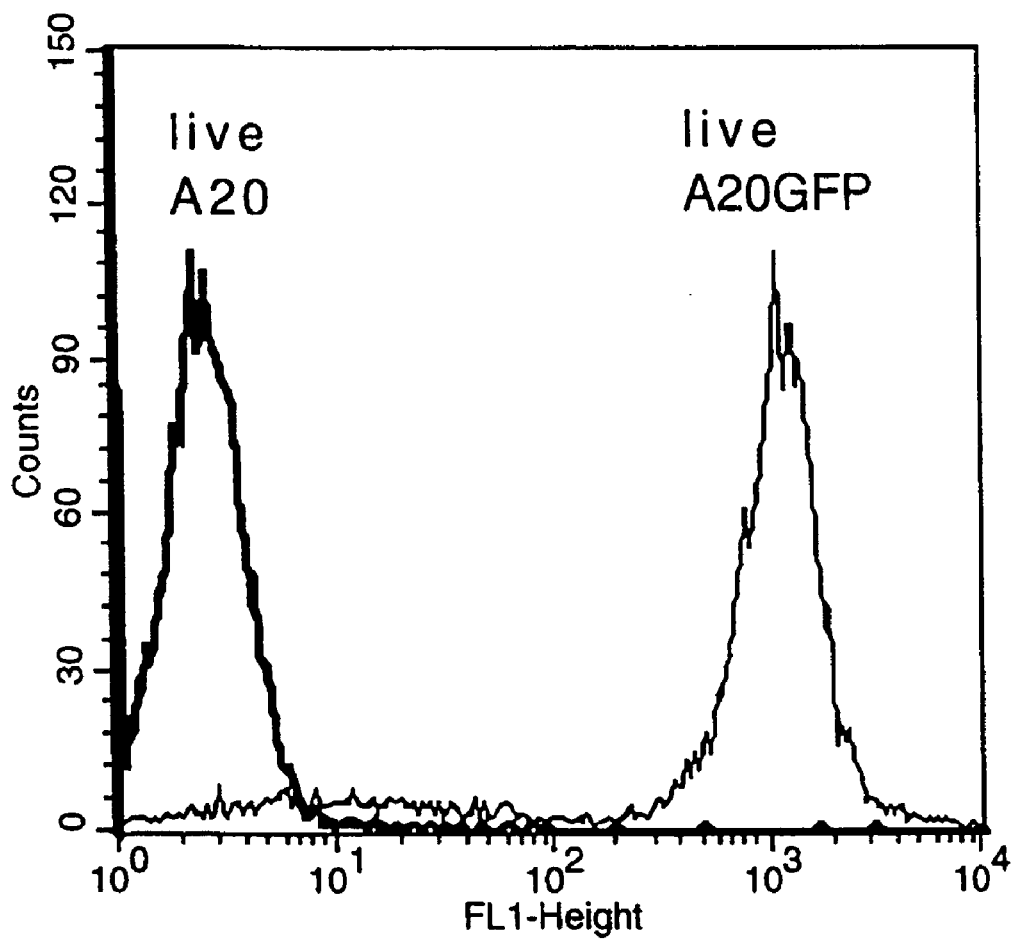
FIG. 4: FACS-histogramm showing the difference of the fluorescing capacities between non-transfected living A20 and GFP-transfected living A20GFP measured on the FL-1 channel.
Figure 5:
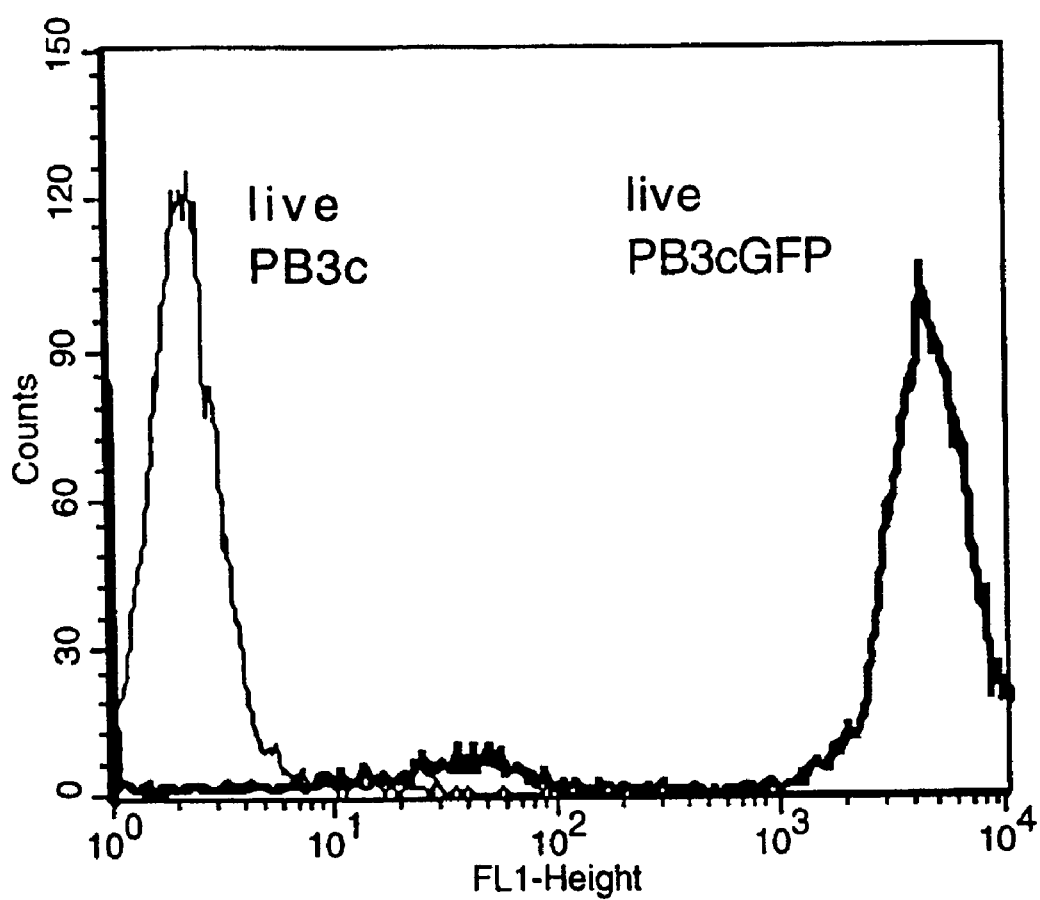
FIG. 5: FACS-histogramm showing the difference of the fluorescing capacities between non-transfected living PB3c and GFP-transfected living PB3cGFP measured on the FL-1 channel.

For the construction of the pEGFP-N1+MoLV-LTR plasmid (see FIG. 3) the MoLV-LTR promoter[33] (from Gem-MoLV-LTR) was cloned into the Hind III and Eco RI predigested pEGFP-N1 vector (from Clontech).

The MoLV-LTR promoter[33] was cloned with Hind III and Eco RI into the pGEM-3Zf(+) vector (from Pro-mega). The Gem-MoLV-LTR contains a unique Hind III and a unique Eco RI restriction site. The resulting MoLV-LTR promoter fragment, after Eco RI and Hind III digestion, has a length of 697 bp, whereas the other resulting fragment corresponds to the pGEM-3Zf(+) backbone.

The pEGFP-N1 (from Clontech) contains a unique Hind III restriction site (position 623) and a unique Eco RI restriction site (position 630). The two resulting fragments, after Hind III and Eco RI digestion, have a length of 4726 bp and 7 bp, respectively.

Of pEGFP-N1 7.3 μg were pipetted in an Eppendorf tube (tube A) together with 1 μl Hind III, 3 μl 1-10× incubation buffer for restriction enzyme B (from Boehringer Mannheim) and 21 μl double distilled water to make a final volume of 30 μl. The tube was incubated for 3 hours at 37° C. Afterwards, it was incubated at 65° C. for 5 minutes, cooled down at 37° C. and 9 μl double distilled water, 1 μl 10× incubation buffer for restriction enzyme B and 1 μl Eco RI were added to the mixture making a final volume of 40 μl. In another Eppendorf tube (tube B), 3 μg Gem-MoLV-LTR were mixed with 1 μl Hind III, 1 μl Eco RI (from Boehringer Mannheim, 10 U/μl), 3 μl 10× incubation buffer for restriction enzyme B and 20 μl double distilled water making a final volume of 30 μl. Both Eppendorf tubes (tubes A and B) were incubated for 3 hours at 37° C. After incubation, 14 μl DNA-loading buffer were added to both tubes and thereafter the contents were loaded into separate slots on a 0.6% low-melting-point (LMP) agarose gel. In a third slot, 15 μl 1 Kb DNA-ladder (from Promega), diluted 1:3 with DNA-loading buffer, were loaded on the gel. The gel was run at 60–70 Volts for 60–90 minutes. The ethidiumbromide stained DNA-bands in the gel were visualized with 300 nm UV-light and their sizes were determined relative to the 1 Kb DNA-ladder. The DNA-band containing the 697 bp long fragment from the digested Gem-MoLV-LTR vector and the DNA-band containing the 4726 bp long fragment from the digested pEGFP-N1 were cut out from the LMP agarose gel and put into two different Eppendorf tubes. Both tubes were centrifuged briefly and incubated at 65° C. for 5 minutes. Afterwards, 3.5 µl of the 4726 bp long fragment (Hind III and Eco RI digested pEGFP-N1) were mixed together with 7 µl of the 697 bp long fragment (MoLV-LTR promoter from the Hind III and Eco RI digested Gem-MoLV-LTR) in a separate Eppendorf tube, incubated at 65° C. for 5 minutes and centrifuged briefly. The mixture was cooled at 37° C. and then the following ligation mix was added: 2 µl 10× ligation buffer, 7.5 µl double distilled water and 1 µl T4 DNA ligase. The ligation reaction was incubated overnight at 15° C.

The newly ligated pEGFP-N1+MoLV-LTR was transformed into One Shot™ competent *E. coli* (from Invitrogen), according to the manufacturer protocol of Invitrogen.

10 µl of the ligation reaction were used for the transformation of competent *E. coli*. 50, 100 and 200 µl of the transformation mixture were plated on different kanamycin-containing LB agar plates (final concentration of kanamycin: 50 µg/ml) and the plates were then incubated at 37° C. overnight. The next day different bacterial colonies were picked for further analysis of recombinant DNA clones by small-scale plasmid DNA isolation (according to the alkaline lysis method described in Maniatis et al.[7]).

To check the presence of the MoLV-LTR promoter fragment cloned into pEGFP-N1, a Hind III and Eco RI restriction enzyme digestion of the isolated DNA was carried out (3 µl 10× incubation buffer for restriction enzyme B. 5 µl plasmid DNA from the alkaline lysis method, 22 µl double distilled water, 1 µl Hind III, 1 µl Eco RI were mixed together in an Eppendorf tube and incubated for 3 hours at 37° C.), loaded on a 1% agarose gel and subsequently visualized with 300 nm UV-light and analyzed. The expected fragment of 697 bp length after Hind III and Eco RI digestion was observed, and therefore confirmed the presence of the cloned fragment (see FIG. 3).

In order to obtain large quantities of the newly created plasmid, a large-scale plasmid DNA isolation has been performed according to the Qiagen Plasmid Maxi Protocol.

Essentially the same method was used for the construction of the pEGFP-N1+MoLV-LTR vector containing a hygromycin gene (FIG. 16), with the following changes. First, the MoLV-LTR promoter (from pLXSN, Clontech) was cloned into the pEGFP-N1 vector with Sma I and Sac II. Second, the hygromycin gene including a TK promotor and a TK poly A (from pREP4 (Invitrogen) digested with Nru I) was cloned into the Ase I predigested pEGFP-N1+MoLV-LTR vector.

EXAMPLE 3

Preparation of the Cell Line A20GFP by Electroporation of the Murine Cell Line A20.2J with pBluescriptIIKS(+)+EF-1α+EGFP The A20.2J cell line (A20.2J is a BALB/c B cell lymphoma[29-30] from ATCC TIB 208, American Type Culture Collection) was co-electroporated with the pBluescriptIIKS(+)+EF-1α+EGFP and pSV2neo (plasmid containing the neo gene which confers resistance to the drug G418). 3×10⁷ cells (A20.2J) were required for the electroporration and were plated into fresh medium complete (Iscove's modified Dulbecco's medium (from Gibco BRL) supplemented with 5% fetal calf serum (from Gibco BRL), 0.05 mM 2-mercaptoethanol (from Gibco BRL) and 2 mM L-glutamine (from Gibco BRL)) one day prior to the poration. Before electroporation, the cells were washed three times in ice-cold $Ca^{2+}/Mg^{2+}$ free PBS (phosphate buffered saline: 8 g NaCl, 0.2 g KCl, 1.44 g $Na_2HPO_4$, 0.24 g $KH_2PO_4$ in 800 ml double distilled water, adjusted to pH 7.4 with HCl and double distilled water was added to a final volume of 1 liter), counted and 3×10⁷ cells were resuspended in 800 µl ice-cold PBS. 60 µg pBluescript-IIKS (+)+EF-1α+EGFP and 6 µg pSV2neo were aliquoted into an electroporation cuvette for the co-electroporation of A20.2J. The chilled cells were added to the DNA solution in the electroporation cuvette. The cells and the DNA solution were mixed by pipetting and incubated on ice for 15 minutes. After incubation, the DNA cell suspension was subjected to an electric pulse of 960 µF and 300 V delivered by a BioRad Gene Pulser™. After electroporation, the cells were kept on ice for 15 minutes, followed by a 15 minutes incubation at room temperature. The electroporated A20.2J were then transferred to culture medium (medium complete) and grown for 24 hours before transfectants were selected in medium complete supplemented with G418 (1 mg/ml, from Gibco BRL).

The electroporated cells were cultured in the selection medium (medium complete supplemented with G418) for 2–4 weeks, analyzed under the fluorescence microscope and then a single-cell-assay was performed in order to obtain a clonally and stably GFP-transfected cell line named A20GFP.

EXAMPLE 4

Preparation of the Cell Line PB3cGFP by Electroporation of the Murine Cell Line PB-3c with pEGFP-N1+MoLV-LTR The PB-3c cell line (which is a cloned, strictly IL-3 dependent, non tumorigenic mastocyte line isolated from the bone marrow of a DBA/2 mouse[31]) was electroporated with pEGFP-N1+MoLV-LTR. 3×10⁷ cells (PB-3c) were required for the electroporation and were plated into fresh medium (medium complete supplemented with 2% IL-3) one day prior to the poration. Before electroporation, the cells were washed three times in ice-cold $Ca^{2+}/Mg^{2+}$ free PBS, counted and 3×10⁷ cells were resuspended in 800 µl ice-cold PBS. 10 µg pEGFP-N1+MoLV-LTR were aliquoted into an electroporation cuvette for the electroporation of PB-3c. The chilled cells were added to the DNA solution in the electroporation cuvette. The cells and the DNA solution were mixed by pipetting and incubated on ice for 15 minutes. After incubation, the DNA cell suspension was subjected to an electric pulse of 960 µF and 300 V delivered by a BioRad Gene Pulser™. After electroporation, the cells were kept on ice for 15 minutes, followed by a 15 minutes incubation at room temperature. The electroporated PB-3c cells were then transferred to culture medium (medium complete supplemented with 2% IL-3) and grown for 48 hours before transfectants were selected in medium complete supplemented with 2% IL-3 and G418 (1 mg/ml, from Gibco BRL).

The electroporated cells were cultured in the selection medium for 2–4 weeks, analyzed under the fluorescence microscope and then a single-cell-assay was performed in order to obtain a clonally and stably GFP-transfected cell line named PB3cGFP.

EXAMPLE 5

Preparation of the Cell Line JurkatGFP by Electroporation of the Human Cell Line Jurkat with pEGFP-N1+MoLV-LTR The Jurkat cell line (Jurkat is a human acute T cell leukemia from ATCC TIB 152) was electroporated with pEGFP-N1+MoLV-LTR. 3×10⁷ cells (Jurkat) were required for the electroporation and were plated into fresh RPMI medium (RPMI 1640 medium (from Gibco BRL) supplemented with 5% fetal calf serum (from Gibco BRL), 0.05 mM 2-mercaptoethanol (from Gibco BRL) and 2 mM L-glutamine (from Gibco BRL)) one day prior to the poration. Before electroporation, the cells were washed three times in ice-cold $Ca^{2+}/Mg^{2+}$free PBS, counted and 3×10⁷ cells were resuspended in 800 µl ice-cold PBS. 10 µg pEGFP-N1+MoLV-LTR were aliquoted into an electroporation cuvette for the electroporation of Jurkat. The chilled cells were added to the DNA solution in the electroporation cuvette. The cells and the DNA solution were mixed by pipetting and incubated on ice for 15 minutes. After incubation, the DNA cell suspension was subjected to an electric pulse of 960 µF and 300 V delivered by a BioRad Gene Pulser™. After electroporation, the cells were kept on ice for 15 minutes, followed by a 15 minutes incubation at room temperature. The electroporated Jurkat cells were then transferred to culture medium (RPMI medium) and grown for 48 hours before transfectants were selected in RPMI medium supplemented with G418 (1 mg/ml, from Gibco BRL).

The electroporated cells were cultured in the selection medium (RPMI medium supplemented with G418) for 2–4 weeks, analyzed under the fluorescence microscope and then a single-cell-assay was performed in order to obtain a clonally and stably GFP-transfected cell line named Jurkat-GFP.

EXAMPLE 6

Comparison of the Fluorescent Capacities of Non-transfected and GFP-transfected Cells Four non-related cell lines (A20.2J, PB-3c, Jurkat and DM) were chosen in order to study the fluorescing capacities.

After stable transfection of the four different cell lines with a GFP-carrying vector, the non-transfected cells were compared with the GFP-transfected cells of each cell line on behalf of their fluorescing capacities, measured by flow cytometric analysis in a FACScan (Becton Dickinson, San Jose, USA). The software program Cell Quest (Becton Dickinson, USA) was used to acquire the data. The FACScan was calibrated with Calibrite beads from Becton Dickinson prior to acquisition. The following parameters were measured:

FSC-Height (forward scatter) as a measure for the cell size

SSC-Height (side scatter) as a measure for the internal granularity (density)of the cells, green fluorescence (e.g. GFPmut1) was visualised on the FL-1 channel in the FACScan Orange fluorescence (e.g. propidium iodide) was visualised on the FL-2 channel in the FACScan For measurements, 10000 cells were acquired from each FACS-tube containing 250000 cells.

Figure 15:
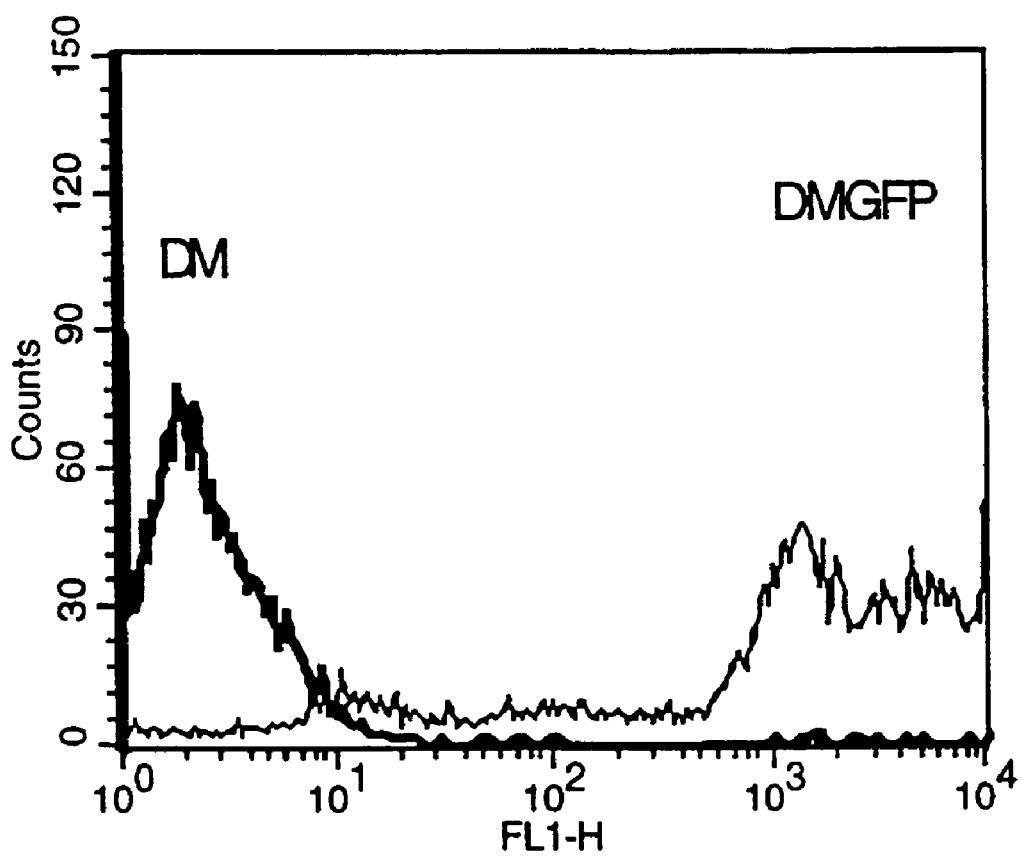
FIG. 15: FACS-histogramm showing the difference of the fluorescing capacities between non-transfected living DM and GFP-transfected living DMGFP measured on the FL-1 channel.

There were two surprising findings: The first was the high fluorescence intensity of the GFP-transfected cells compared to the autofluorescence of the non-transfected ones (FIGS. 4–6 and 15). The second was that the fluorescence-range (visualized on the FL-1 channel in the FACScan) of all tested live GFP-transfected cell lines was narrow (see FIG.): A20GFP (FIG. 4), PB3cGFP (FIG. 5), JurkatGFP (FIG. 6) and DMGFP (FIG. 15). This rules out the problem of high and low GFP expressors.

EXAMPLE 7

Apoptosis Assay: Induction of Apoptosis in A20GFP by sFasL

Apoptosis was induced by an 8 hours incubaton of A20GFP with the sFasL supernatant (sFasL SN has been produced by FasL-transfected N2a cells, which were provided by A. Fontana, University Hospital, Zurich, Switzerland). As negative control, A20GFP incubated in medium complete has been used.

After washing A20GFP cells with PBS, two FACS-tubes (from Falcon) were prepared, each containing 250,000 cells. The cells in the first tube (tube 1) were resuspended in 500 µl normal medium complete as negative control, whereas the cells in the second tube (tube 2) were resuspended in 100 µl apoptosis inducing soluble FasLigand supernatant and 400 µl medium complete to a final volume of 500 µl. Both tubes were incubated for 8 hours at 37° C. After incubation, the cells were washed with PBS, centrifuged at 1400 rpm for 5 minutes, taken up in 500 µl PBS and measured in the FACScan.

Figure 8A:
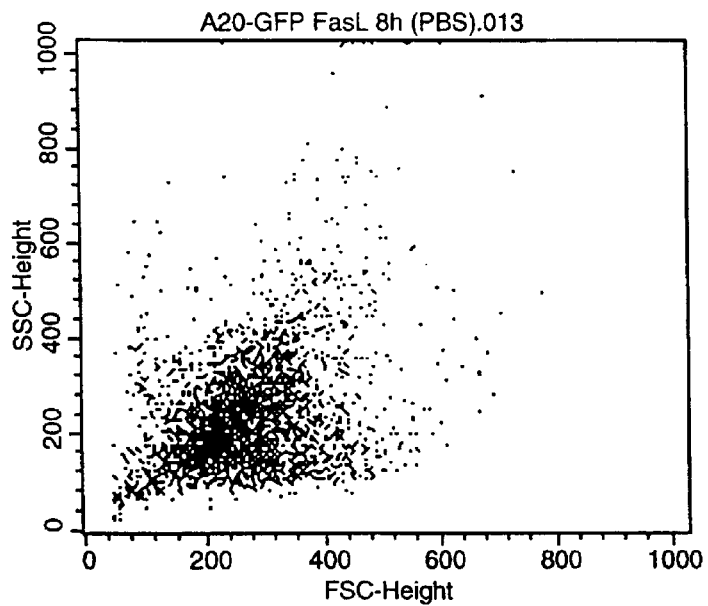
FIG. 8a: FACS dot plot showing the shrinkage and increased granular density (compared to FIG. 7a) of sFasL SN treated and therefore mainly apoptotic A20GFP.
Figure 8B:
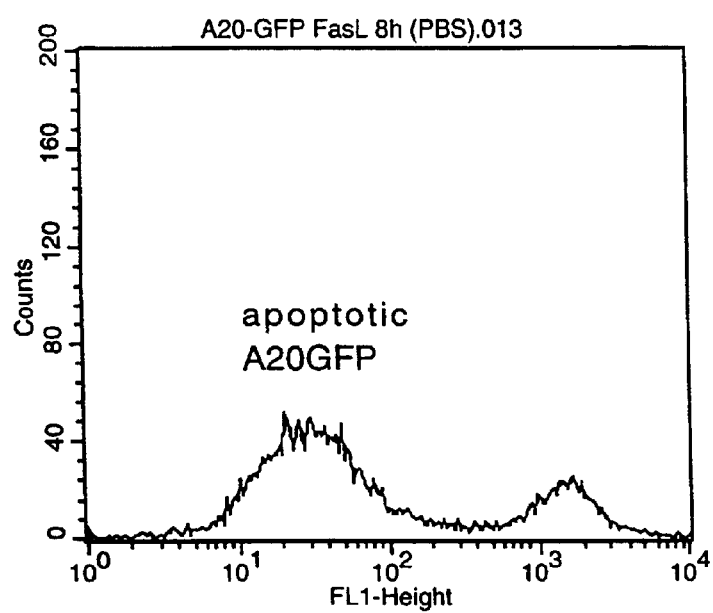
FIG. 8b: FACS-histogramm showing the decrease of GFP associated fluorescence in sFasL SN treated and therefore mainly apoptotic A20GFP.
Figure 8C:
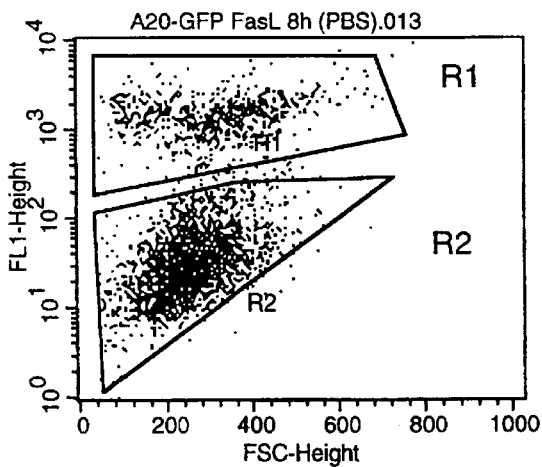
FIG. 8c: FACS dot plot showing the difference between high fluorescing living A20GFP (R1) and low fluorescing apoptotic A20GFP (R2).
Figure 8D:
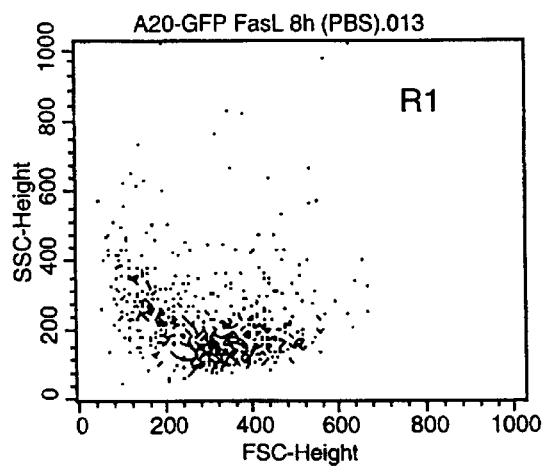
FIG. 8d: FACS dot plot of high fluorescing living A20GFP (gate R1 from FIG. 8c). The high fluorescing A20GFP cells (R1) belong mainly to the not shrunken and not granular dense cell population (typical pattern of living cells).
Figure 8E:
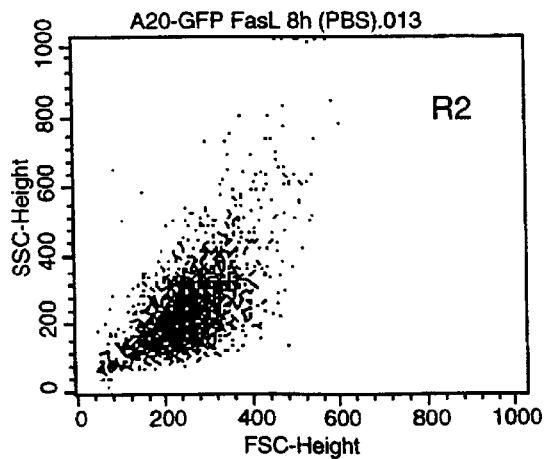
FIG. 8e: FACS dot plot of low fluorescing apoptotic A20GFP (gate R2 from FIG. 8c). The low fluorescing A20GFP cells belong mainly to the shrunken and granular dense cell population (typical feature of apoptotic cells).
Figure 9A:
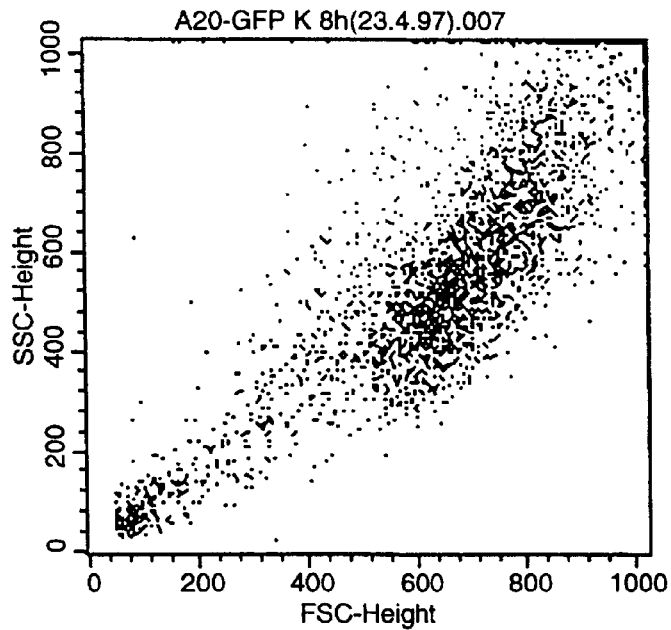
FIG. 9a: FACS dot plot showing the cell size and granularity pattern of living A20GFP (ethanol treated and PI-stained).
Figure 9B:
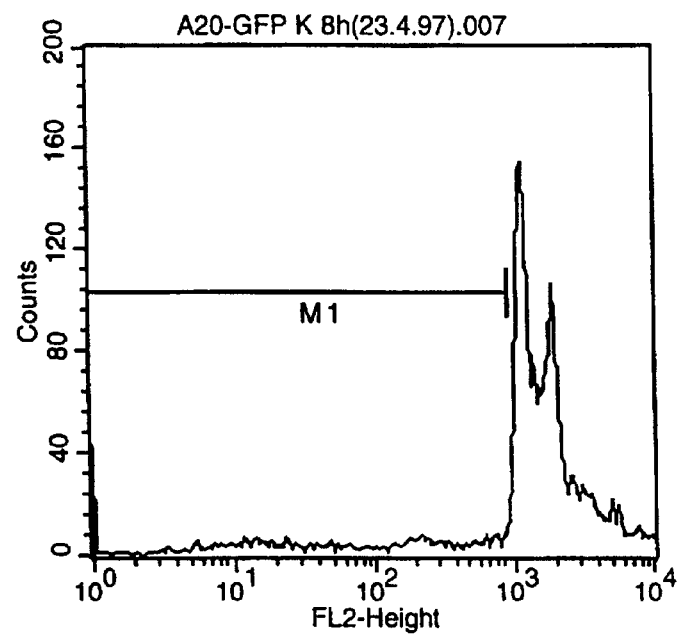
FIG. 9b: FACS-histogramm showing the typical DNA-pattern of PI-stained living A20GFP.

In the control tube (tube 1), the majority of the cells showed a high GFP-associated fluorescence (FIGS. 7a and 7b), whereas in the tube containing the sFasL SN treated cells (tube 2) a majority of low fluorescing cells was found after 8 hours incubation (FIGS. 8a and 8b). These low fluorescing cells corresponded to the shrunken apoptotic cell population (FIGS. 8c and 8e), in contrast to the high fluorescing cells, that are mainly found in the bigger and less granular living cell population (FIGS. 8c and 8d).

To further show and confirm, that the low fluorescing cell population corresponds to the apoptotic shrunken cell population, a propidium iodide staining for intracellular DNA has been performed with the remaining cells of the previously measured tubes (tube 1 and 2). The cells were first washed with PBS, then incubated in 70% ethanol at −20° C. for 2 hours, washed again with PBS and stained with 500 µl PI-solution (50 µg PI in 1 ml PBS) for 30 minutes at 37° C. Both tubes (tube 1 and 2), containing PI stained cells, were immediately measured in the FACScan.

Figure 10A:
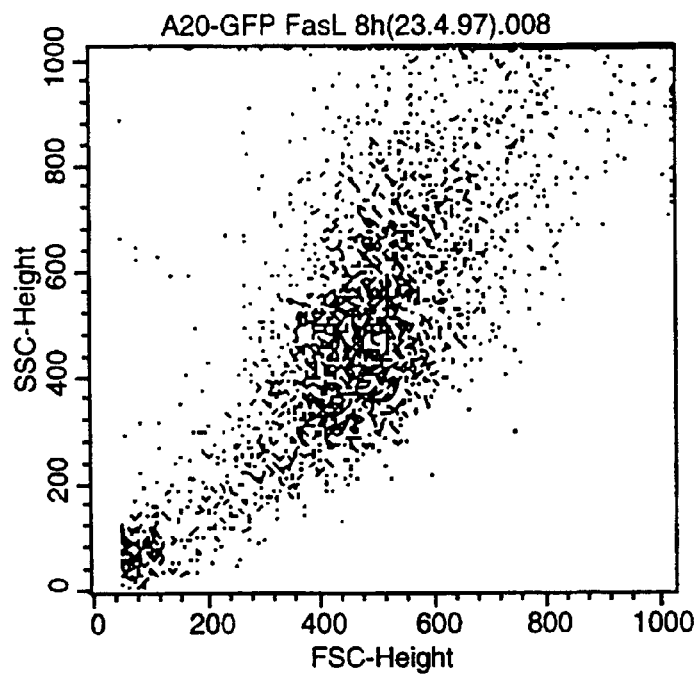
FIG. 10a: FACS dot plot showing the shrinkage of sFasL SN treated A2OGFP (ethanol treated and PI-stained).
Figure 10B:
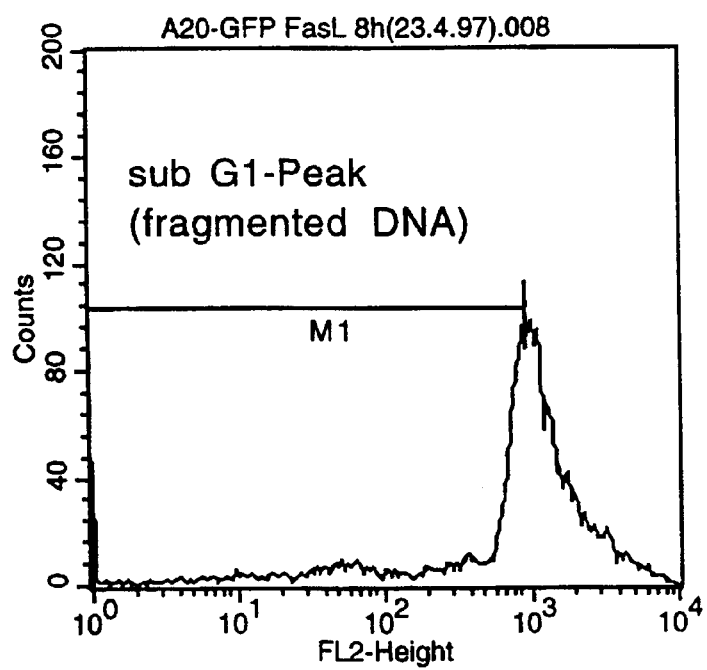
FIG. 10b: FACS-histogramm showing the fragmentation of DNA (represented by the sub-G1 peak=M1), as proof for apoptosis in sFasL SN treated A20GFP.

The DNA profile of the apoptosis inducing sFasL SN treated cells (tube 2) was considerably changed after 8 hours incubation (FIGS. 10a and 10b). The majority of the DNA has been fragmented (visualized as sub-G1 peak on the FL-2 channel in a FACScan, FIG. 10b), in comparison to the control (tube 1, see FIGS. 9a and 9b), confirming the result of massive apoptosis induced by sFasL SN.

Furthermore, the cell population with fragmented DNA corresponded to the group of the shrunken apoptotic and low fluorescing cells.

In conclusion, apoptotic cells shrink, they have mainly (but not completely) lost the GFP-associated fluorescence and have a fragmented DNA (which is a specific characteristic of apoptosis). Moreover, the amount of apoptotic cells seen with the PI method was comparable to the amount detected with the GFP method (data not shown).

EXAMPLE 8

Toxicity Assay: Induction of Necrosis in A20GFP

A20GFP cells were first washed with PBS and then 250000 cells incubated in a FACS-tube with 100 µl anti-A20 polyclonal antibody for 60 min at 4° C. After incubation, the cells were washed with PBS, resuspended in 50 µl rabbit complement (Readysystem) and incubated in a 37° C.

watherbath for 1 hour. The cells were washed again with PBS and resuspended in 500 µl PBS and immediately measured in a FACScan. As controls, untreated (without complement) A20GFP and A20 cells were used.

Figure 11:
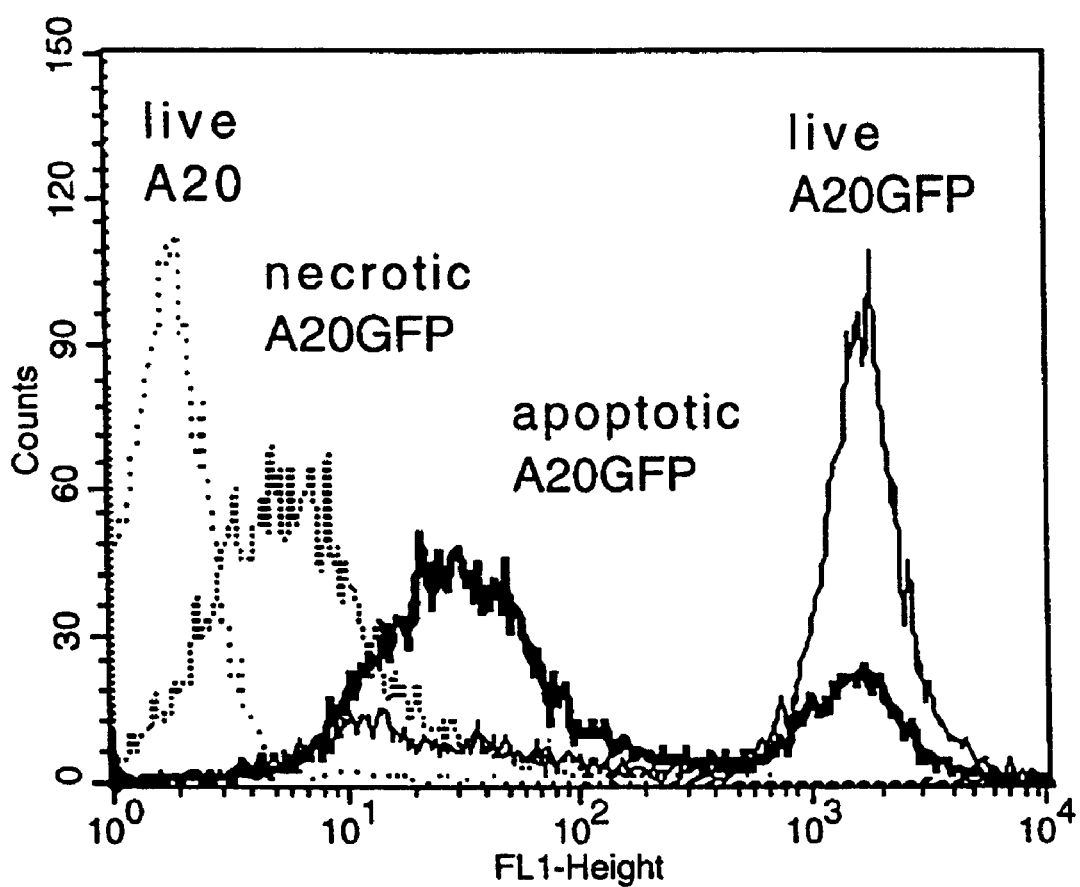
FIG. 11: FACS-histogramm showing the fluorescence intensity of living A20GFP compared to apoptotic A20GFP, necrotic A20GFP and living non-transfected A20.

Complement binding induces necrosis in target cells. This assay was thus performed in order to evaluate the fluorescing capacity of necrotic cells. The findings were striking, as necrotic cells completely lost their GFP-associated fluorescence capacity within an hour. Thus complement treated A20GFP cells can hardly be distinguished from non-transfected live A20 cells (FIG. 11). The necrotic cells can be distinguished from apoptotic cells, the latter still express low fluorescing capacity (e.g. 8 hours after sFasL SN treatment, as shown in the example described before). This makes the GFP-assay a useful tool to distinguish between necrotic, apoptotic and live GFP-transfected cells (FIG. 11).

EXAMPLE 9

Inhibition of De novo RNA Synthesis by Actinomycin D (ActD), Protein Synthesis by Cycloheximide (CHX) and the Potential Role of Interfering with the GFP Apoptosis Assay in A20GFP To find out whether the fluorescence of A20GFP and the GFP apoptosis assay as described in example 7 is dependent on the de novo transcription and protein synthesis, Act D (pharmacy of the University Hospital, Basel), a RNA synthesis inhibitor, and Cycloheximide (Sigma), a protein synthesis inhibitor, were tested in our experimental protocol. After washing A20GFP cells with PBS, 250000 cells were aliquoted in FACS-tubes and incubated with:

a) Tube 1 (control): 500 µl medium complete (MC)
b) Tube 2: 100 µl sFasL SN and 400 µl MC
c) Tube 3: 500 µl MC and 5 µg/ml ActD
d) Tube 4: 400 µl MC, 100 µl sFasL SN, 5 µg/ml ActD
e) Tube 5: 500 µl MC and 10 µg/ml CHX
f) Tube 6: 400 µl MC, 100 µl sFasL SN and 10 µg/ml CHX
g) Tube 7: 500 µl MC, 5 µg/ml Act D and 10 µg/ml CHX
h) Tube 8: 400 µl MC, 100 µl sFasL SN, 5 µg/ml Act D and 10 µg/ml CHX Tubes 1–8 (a–h) were incubated for 10 hours at 37° C. The fluorescing status of the cells was assayed at 10 hours post treatment.

Figure 12A:
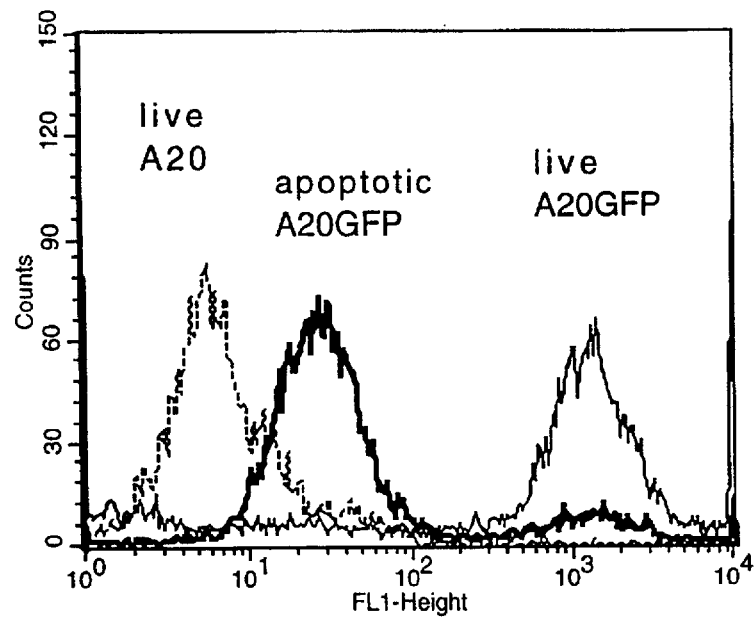
FIG. 12a: FACS-histogramm showing the induction of apoptosis by sFasL SN in A20GFP (control experiment to FIG. 12b).
Figure 12B:
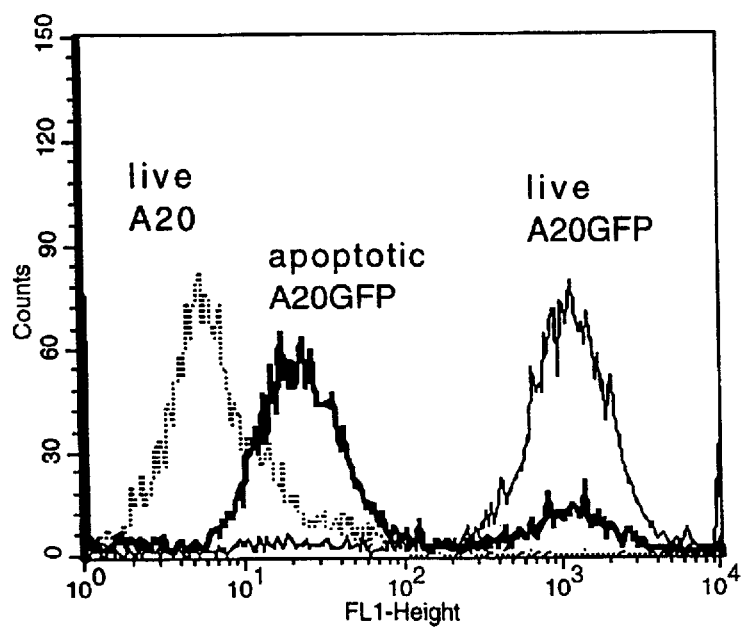
FIG. 12b: FACS-histogramm showing the induction of apoptosis by sFasL SN in A20GFP in the presence of ActD and CHX. Neither a reduction of GFP-associated fluorescence nor a inhibition of apoptosis can be observed.

As seen in FIGS. 12a and 12b, there is no difference between the fluorescence intensity of untreated A20GFP (FIG. 12a) compared to A20GFP treated with ActD and/or CHX (FIG. 12b). sFasL SN treatment of A20GFP induces apoptosis to the same extent, whether the cells were ActD- and/or CHX-treated or not. In conclusion, ActD and CHX, either alone or together, do not substantially interfere with the fluorescing capacity of A20GFP nor do they inhibit sFasL SN induced apoptosis after 10 hours of treatment. Therefore, A20GFP, in order to fluorescence, do not require de novo transcription and translation during the 10 hours.

EXAMPLE 10

Apoptosis Assay: Induction of Apoptosis in PB3cGFP by Interleukin-3 Deprivation

PB3cGFP is an interleukin-3 (IL-3) dependent cell line. The addition of IL-3 to the culture medium (medium complete) prevents the PB3cGFP cells from under-going apoptosis (IL-3 as an anti-apoptotic compound). In contrast, upon IL-3 deprivation a strong apoptotic response is seen within 12 hours.

For this experiment, 250000 PBS-washed PB3cGFP cells were aliquoted in two different FACS-tubes.

Tube A: contained the cells and MC supplemented with IL-3.

Tube B: contained the cells and MC without IL-3.

Both tubes were incubated for 12 hours at 37° C.

The GFP-associated fluorescence of the PB3cGFP cells was measured after 12 hours of IL-3 deprivation.

Figure 13:
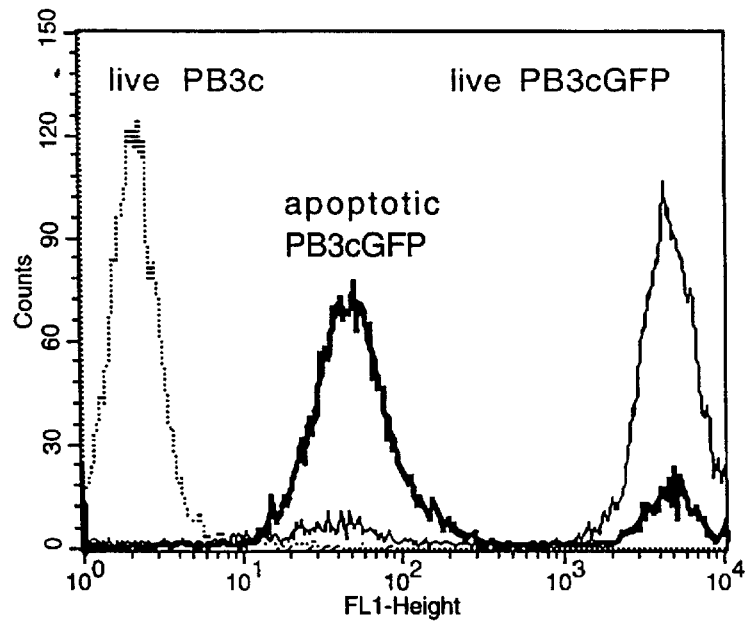
FIG. 13: FACS-histogramm showing the anti-apoptotic effect of IL-3 treatment. Apoptotic PB3cGFP cells show a lower GFP-associated fluorescence intensity compared to the IL-3 treated and therefore living PB3cGFP.

As expected, and seen with A20GFP, very similar results were obtained with PB3cGFP. PB3cGFP, cultured in MC supplemented with IL-3 (tube A), showed a high GFP-associated fluorescence, whereas IL-3 deprived PB3cGFP cells (tube B) underwent apoptosis and demonstrated a low GFP-associated fluorescence intensity, making them clearly distinguishable from live PB3cGFP and live PB3c cells (FIG. 13). These findings have been confirmed by the PI staining method, as it has been described with the A20GFP cells (data not shown).

EXAMPLE 11

Apoptosis Assay: Induction of Apoptosis in JurkatGFP by sFasL SN

This apoptosis assay has also been performed with sFasL SN, a known cell death inducer in Jurkat cells. 250000 PBS-washed JurkatGFP cells were aliquoted in two different FACS-tubes.

Tube 1 (control): cells were incubated with 500 µl RPMI medium

Tube 2: cells were incubated with 100 µl sFasL SN and 400 µl RPMI medium

Both tubes were incubated for 18 hours at 37° C. In this experiment cells were immediately measured after incubation, without prior washing with PBS.

As expected, and seen with A20GFP and PB3cGFP cells, very similar results were obtained.

Figure 14:
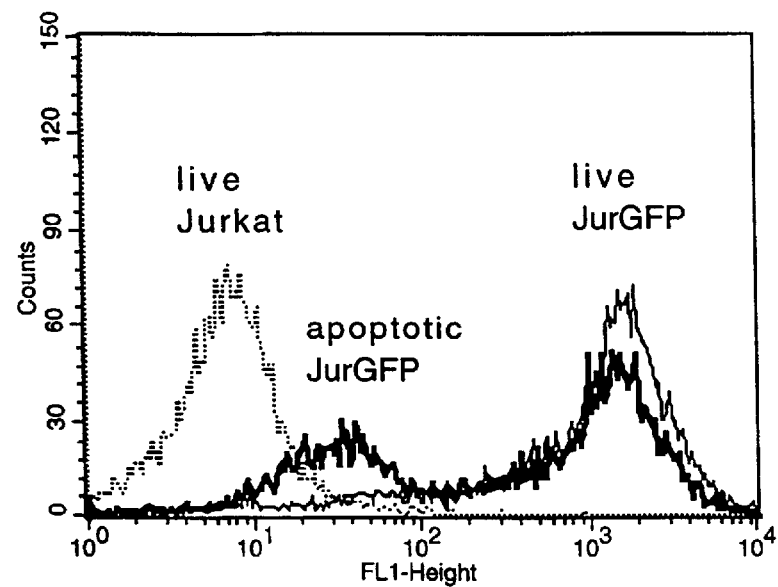
FIG. 14: FACS-histogramm showing the pro-apoptotic effect of sFasL SN on JurkatGFP, visualized as a decrease of GFP-associated fluorescence in apoptotic JurkatGFP cells compared to living JurkatGFP.

As shown in FIG. 14, sFasL SN induced apoptosis. GFP-associated fluorescence was high in live JurkatGFP, whereas the apoptotic JurkatGFP cells had a marked reduced GFP-associated fluorescence, but were still distinguishable from non-transfected live Jurkat cells. These findings have been confirmed by the PI staining method.

In relation to the previous experiment, the present results show that it is not necessary to wash the cells with PBS before measuring. This may be particularly useful for large screening assays, where individual tubes cannot be separately washed.

EXAMPLE 12

Apoptosis Assay: Induction of Apoptosis in JurkatGFP by Recombinant Human TRAIL

This apoptosis assay has been performed with recombinant human TRAIL, a known cell death inducer in Jurkat cells. 250,000 JurkatGFP cells were aliquoted in two different FACS-tubes.

Tube 1: (control): cells were incubated with 500 µl RPMI medium,

Tube 2: cells were incubated with 25 µl recombinant human TRAIL and 475 µl RPMI medium.

Both tubes were incubated for 18 hours at 37° C. After incubation the test tubes were immediately measured without prior washing.

Figure 6A:
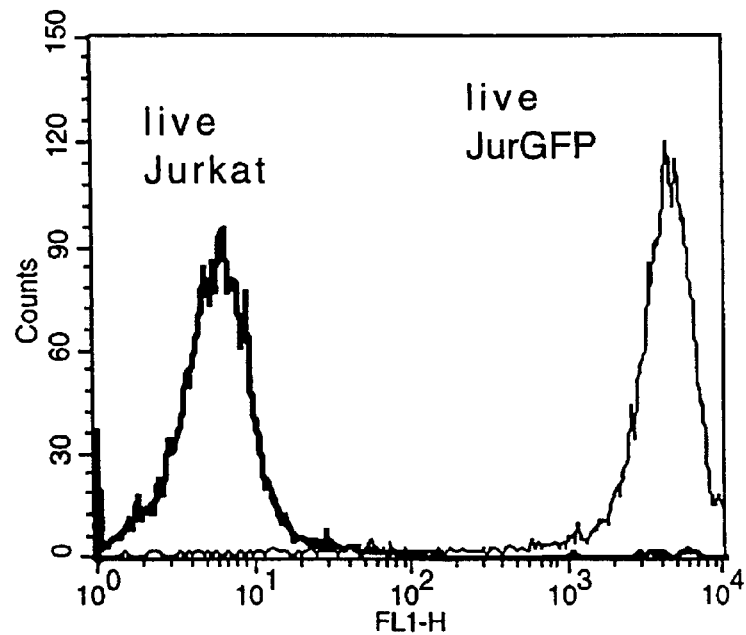
FIG. 6a: FACS-histogramm showing the difference of the fluorescing capacities between non-transfected living Jurkat and GFP-transfected living JurkatGFP measured on the FL-1 channel.
Figure 6B:
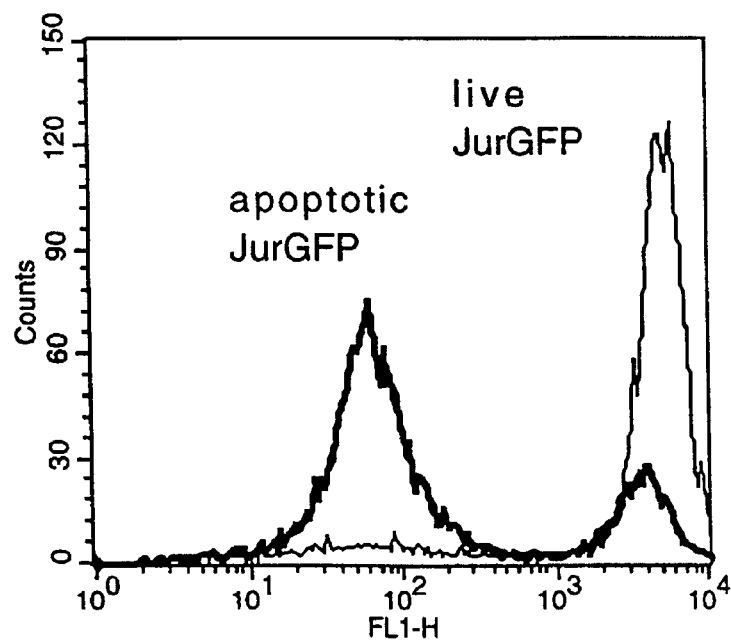
FIG. 6b: FACS-histogramm showing the fluorescence intensity of living JurkatGFP compared to apoptotic JurkatGFP (induced by recombinant human TRAIL)
Figure 7A:
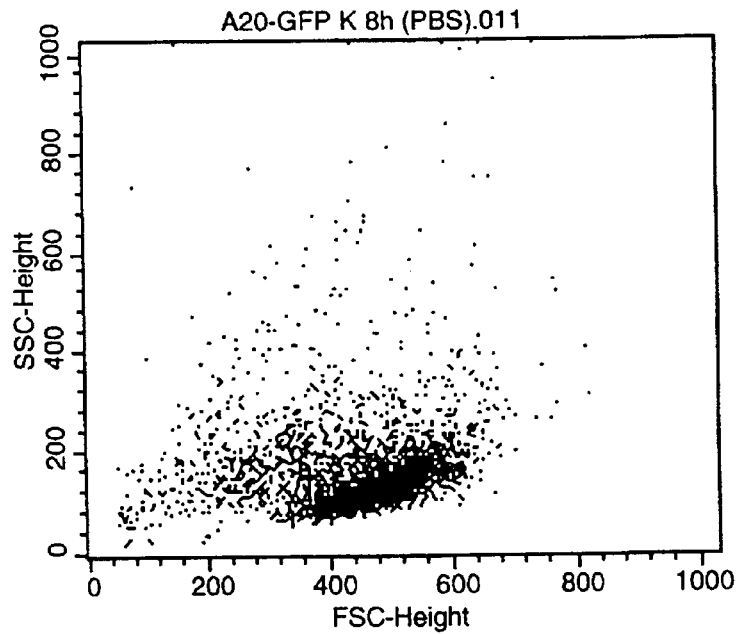
FIG. 7a: FACS dot plot showing the cell size (FSC) and granularity (SSC) of living A20GFP.
Figure 7B:
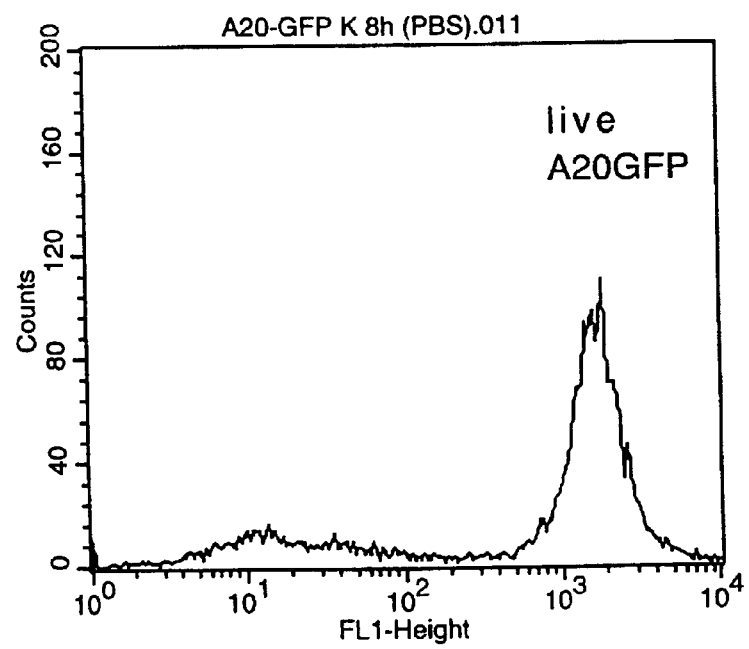
FIG. 7b: FACS-histogramm showing the typical GFP-associated fluorescence profile of living A20GFP.

Like sFasL SN, recombinant human TRAIL induced apoptosis in JurkatGFP cells (FIG. 6b) in a dose dependent manner (data not shown). FIG. 6b shows a similar profile as already observed with A20GFP (FIG. 11) and PB3cGFP (FIG. 13) cells after induction of apoptosis by sFasL SN or IL-3 deprivation, respectively.

EXAMPLE 13

Preparation of Cell Line DMGFP by Transfection of the Human Melanoma Cell Line DM with pEGFP-N1+MoLV-LTR The human melanoma cell line DM 35 was transfected with pEGFP-N1+MoLV-LTR.

$10^6$ DM cells were plated out one day prior to the transfection in a 10 cm diameter culture dish containing complete medium including 10% FCS. 10 μg pEGFP-N 1+MoLV-LTR were mixed together with 20 μl SuperFect Reagent (Qiagen AG, Switzerland) and 120 μl complete medium w/o FCS and incubated for 30 minutes at room temperature. After incubation, 1 ml complete medium containing FCS were added and the whole mixture was poured onto the dish already containing DM cells in 10 ml complete medium. 48 hours after transfection, cells were washed once with complete medium and further cultivated in selective medium containing 1 mg/ml G418 (Gibco BRL) for 3 weeks until single clones became visible. These clones were analyzed under the fluorescence microscope. Positive clones were further cultivated in 24 well plates in selective medium and analyzed again for the expression of the transgene. Single-cell assay was then performed in order to obtain single clones stably expressing the GFP transgene.

Abbreviations

The following abbreviations are used through-out out the description:

| | |
|---|---|
| ActD | Actinomycin D |
| bp | base pairs |
| CHX | Cycloheximide |
| DIG | Digoxygenin |
| ds DNA | double-stranded DNA |
| EDTA | Ethylenediaminetetraacetic acid |
| EF-1α | elongation factor-1α |
| FACS | Fluorescence Activated Cell Sorter |
| FCS | fetal calf serum |
| FITC | Fluorescein isothiocyanate |
| FL-1 | Fluorescence channel 1 (detects fluorescence emission in the range of 530 (+/−25) nm |
| FSC | Forward Scatter (cell size) |
| GFP | Green Fluorescent Protein |
| IL-3 | Interleukin-3 |
| LMP | low melting point |
| MC | medium complete |
| PBS | phosphate buffered saline |
| PI | propidium iodide |
| sFasL | soluble Fas Ligand |
| SN | supernatant |
| SSC | Side Scatter (granularity of cells) |
| ss DNA | single-stranded DNA |
| TAE | Tris(hydroxymethyl)aminoethane |
| TNF | Tumor Necrosis Factor |
| TRAIL | TNF-related apoptosis inducing ligand |
| TRAIL-R | TNF-related apoptosis inducing ligand receptor |
| TUNEL | TdT-mediated end labeling of DNA |

REFERENCES

1. Wyllie, A. H., Kerr, J. F. R. & Currie, A. R. *Int. Rev. Cytol.* 68, 251 (1980).
2. Arends, M. J. & Wyllie, A. H. *Int. Rev. Exp. Pathol.* 32, 223 (1991).
3. Wyllie, A. H. *Nature* 284, 555 (1980).
4. Roy, C., et al. *Exp. Cell Res.* 200, 416 (1992).
5. Itoh, N., et al. *Cell* 66, 233–43 (1991).
6. Watanabe, F. R., et al. *J. Immunol.* 148, 1274–9 (1992).
7. Oehm, A., et al. *J. Biol. Chem.* 267, 10709–15 (1992).
8. Cormack, B. P. et al. *Gene* 173, 33–38 (1996)
9. Trauth, B. C., et al. *Science* 245, 301–5 (1989).
10. Itoh, N., et al. *Cell* 66, 233–43 (1991).
11. Watanabe, F. R., et al. *J. Immunol.* 148, 1274–9 (1992).
12. Ogasawara, J., Suda, T. & Nagata, S. *J. Exp. Med.* 181, 485–91 (1995).
13. Suda, T. & Nagata, S. *J. Exp. Med.* 179, 873–9 (1994).
14. Suda, T., et al. *J. Immunol.* 154, 3806–13 (1995).
15. Vignaux, F., et al. *J. Exp. Med.* 181, 781–6 (1995).
16. Tanaka, M. et al. *Nature Med.* 2, 317–322 (1996)
17. O'Connell, J. et al. *J. Exp. Med.* 184, 1075–1082
18. Hahne, M. et al. *Science* 274, 1363–1366 (1996)
19. Strand, S. et al. *Nature Med.* 2, 1361–1366 (1996)
20. Nicoletti, I. et al. *J. Immunol. Meth.* 139, 271–279 (1991)
21. Gavrieli, Y. et al. *J. Cell Biol.* 119, 493–501 (1992)
22. Vermes, I. et al. *J. Immunol. Meth.* 184, 39–51 (1995)
23. Chalfie, M. et al. *Science* 263, 802–805 (1994)
24. Wang, S. & Hazelrigg, T. *Nature* 369, 400–403 (1994)
25. Prasher, D. C. et al. *Gene* 111, 229–233 (1992)
26. Inouye, S. & Tsuji, F. I. *FEBS Letters* 341, 277–280 (1994)
27. Mizushima, S. & Nagata, S. *Nucleic Acids Research* Vol. 18, No 17, 5322 (1990)
28. Uetsuki, T., Naito, A., Nagata, S. and Kaziro, Y. *J. Biol. Chem.* 264, 5791–5798 (1989)
29. *J. Immunol.* 122, 549–554 (1979)
30. *J. Exp. Med.* 155, 445 (1982)
31. Ball, P. E., Conroy, M. C., Heusser, C., Davis, J. M. and Conscience, J. F. *Differentiation* 24, 74–78 (1983)
32. Maniatis, T., Fritsch, E. F. and Sambrook, J.: Molecular cloning (a laboratory manual) *Cold Spring Harbor Laboratory*, 368–369 (1982)
33. Cepko, C. L, Roberts, B. E. and Mulligan, R. C. *Cell* 37, 1053–1062 (1984)
34. Lamm, Gabor M., Steinlein, Peter, Cotten, Matt, and Christofori, Gerhard, *Nucleic Acids Research*, 1997, Vol.25, No.23, 4855–4857
35. Zhang, R. D. et al. *Cancer Res.* 51, 2029–2035 (1991)
36. Jeremias, I., Herr, I., Boehler, T. and Debatin, K. M. *Eur. J. Immunol.* 28, 143–152 (1998)
37. Li, Yongan, and Horwitz, Marshall S., *Bio Techniques*, 1997, Vol. 23, No. 6, 1026 ff.

What is claimed is:

1. A method for determining and distinguishing whether apoptosis and whether necrosis is occurring in living test cells that comprise a fluorescent marker protein having a signal that changes in response to the line and apoptotic and/or necrotic state of the cells, wherein said method comprises (a) directly measuring the fluorescent signal intensity from the test cells suspected of undergoing apoptosis or necrosis; (b) correlating the signal intensity with (i) the fluorescent signal intensity from test cells not comprising the fluorescent marker protein and not undergoing necrosis or apoptosis and (ii) the fluorescent signal intensity from test cells having the fluorescent marker protein and not undergoing necrosis or apoptosis; (c) determining and distinguishing that (i) necrosis is occurring in test cells having a signal intensity in the same range as the test cells not comprising the fluorescent marker protein and (ii) apoptosis is occurring in test cells having a signal intensity lower than in the test cells comprising the fluorescent marker protein and not undergoing apoptosis or necrosis, but higher than in the test cells not comprising the fluorescent marker protein.

2. The method according to claim 1, wherein said signal is monitored in the presence of a physical stimulus.

3. The method according to claim 2, wherein said physical stimulus comprises a multiplicity of physical stimulus.

4. The method according to claim 2, wherein said fluorescent signal intensity from test cells is measured in cells incubated in the presence or absence of said physical stimulus, and said fluorescent signal intensity from test cells measured in the presence of said physical stimulus is compared to said fluorescent signal intensity from test cells measured in the absence of said physical stimulus.

5. The method according to claim 1, wherein said marker protein is produced in said living test cells after transfection of said test cells with a DNA coding for and expressing said marker protein in said test cells.

6. The method according to claim 5, wherein said transfection is a stable transfection.

7. The method according to claim 1, wherein said marker protein is green fluorescent protein or a fluorescent mutant thereof.

8. The method according to claim 7, wherein said marker protein is GFPmut1.

9. The method according to claim 1, wherein said fluorescent signal intensity from test cells is measured by means of a flow cytometer or a platereader.

10. The method according to claim 1, wherein said living test cells comprise two groups of test cells, each having a defined number of cells, which were transfected with a DNA vector coding for a fluorescent marker protein, such as green fluorescent protein or a fluorescent mutant thereof, incubating one group together with a test compound in a culture medium, stimulating the cells of both groups with an excitation beam, determining the fluorescing intensities of the cells of each group by means of a flow cytometer, and comparing the fluorescing intensity of the cells of the two groups whereby said one group incubated together with a test compound is suspected of undergoing apoptosis or necrosis and the group not incubated together with the test compound is not undergoing necrosis or apoptosis.

11. The method according to claim 10, wherein said fluorescent marker protein is green fluorescent protein or a fluorescent mutant thereof.

12. The method according to claim 1, wherein said marker protein is produced in said living test cells after transfection of said test cells with pBluescriptIIKS(+)+EF-1α+EGFP or pEGFP-N1+MoLV-LTR.

13. The method according to claim 1, wherein said fluorescent signal intensity from test cells is measured in the presence of a test compound.

14. The method according to claim 13, wherein said test compound comprises a multiplicity of compounds.

15. The method according to claim 14, wherein said multiplicity of compounds is obtained by combinatorial chemistry.

16. The method according to claim 13, wherein said fluorescent signal intensity from test cells is measured in cells incubated in the presence or absence of said test compound, and said fluorescent signal intensity from test cells measured in the presence of said test compound is compared to said fluorescent signal intensity from test cells measured in the absence of said test compound.

17. The method according to claim 13 wherein said test compound is a non-, pro- or anti-apoptotically or necrotically active compound.

18. The method according to claim 1, wherein said living test cells are selected from the group consisting of normal cells, infected cells, and cancer cells.

19. The method according to claim 1, wherein said living test cells are selected from the group consisting of cells of the transfected cell lines A20GFP, PB3cGFP, JurkatGFP, and DMGFP.

20. The method according to claim 1, wherein said measuring fluorescent signal intensity from test cells is done by measuring parameters selected from the group consisting of FSC-Height, SSC-Height, and fluorescence of said marker protein.

21. The method according to claim 1, wherein directly the fluorescent signal intensity between test cell populations are evaluated using dot plot or histogram visualization.

* * * * *

UNITED STATES PATENT AND TRADEMARK OFFICE
CERTIFICATE OF CORRECTION

PATENT NO. : 6,723,567 B1
DATED : April 20, 2004
INVENTOR(S) : Thomas Harr et al.

It is certified that error appears in the above-identified patent and that said Letters Patent is hereby corrected as shown below:

Title page,
Item [73], Assignee, please delete "(SE)" and replace with -- (CH) --.

Column 29,
Line 51, please delete "line" and replace with -- live --.

Column 22,
Line 47, please delete "wherein directly the" and replace with -- wherein the --.

Signed and Sealed this

Tenth Day of August, 2004

JON W. DUDAS
*Acting Director of the United States Patent and Trademark Office*